United States Patent
Sheng et al.

(10) Patent No.: US 8,064,642 B2
(45) Date of Patent: Nov. 22, 2011

(54) CONSTRAINED-CURVE CORRELATION MODEL

(75) Inventors: Ye Sheng, San Jose, CA (US); Shutian Li, Foster City, CA (US); Sohail Sayeh, San Ramon, CA (US)

(73) Assignee: Accuray Incorporated, Sunnyvale, CA (US)

( * ) Notice: Subject to any disclaimer, the term of this patent is extended or adjusted under 35 U.S.C. 154(b) by 987 days.

(21) Appl. No.: 12/008,658

(22) Filed: Jan. 10, 2008

(65) Prior Publication Data

US 2009/0180666 A1    Jul. 16, 2009

(51) Int. Cl.
*G06K 9/00*    (2006.01)

(52) U.S. Cl. ...................................... 382/103

(58) Field of Classification Search .................. 382/100, 382/103; 600/425–429; 378/4, 69; 348/169–173
See application file for complete search history.

(56) References Cited

U.S. PATENT DOCUMENTS

| | | | |
|---|---|---|---|
| 5,251,128 A | 10/1993 | Crawford | |
| 5,287,276 A | 2/1994 | Crawford et al. | |
| 5,538,494 A | 7/1996 | Matsuda | |
| 5,727,554 A | 3/1998 | Kalend et al. | |
| 5,764,723 A | 6/1998 | Weinberger | |
| 6,076,005 A | 6/2000 | Sontag et al. | |
| 6,144,875 A * | 11/2000 | Schweikard et al. | 600/427 |
| 6,307,914 B1 | 10/2001 | Kunieda et al. | |
| 6,314,312 B1 | 11/2001 | Wessels et al. | |
| 6,341,179 B1 | 1/2002 | Stoyle et al. | |
| 6,385,286 B1 | 5/2002 | Fitchard | |
| 6,468,265 B1 | 10/2002 | Evans et al. | |
| 6,501,981 B1 | 12/2002 | Schweikard et al. | |
| 6,662,036 B2 | 12/2003 | Cosman | |
| 6,690,965 B1 | 2/2004 | Riaziat et al. | |
| 6,704,691 B2 | 3/2004 | Chiou | |
| 6,731,970 B2 | 5/2004 | Schlossbauer | |
| 6,778,850 B1 | 8/2004 | Adler | |
| 6,804,548 B2 | 10/2004 | Takahashi et al. | |
| 6,841,389 B2 | 1/2005 | Novikov et al. | |
| 6,937,696 B1 | 8/2005 | Mostafavi | |
| 6,973,202 B2 | 12/2005 | Mostafavi | |
| 7,085,342 B2 | 8/2006 | Younis et al. | |
| 7,171,257 B2 | 1/2007 | Thomson | |
| 7,237,556 B2 | 7/2007 | Smothers et al. | |
| 7,367,955 B2 | 5/2008 | Zhang et al. | |
| 7,668,585 B2 | 2/2010 | Green | |
| 7,822,176 B2 | 10/2010 | Yi et al. | |
| 2001/0014772 A1 | 8/2001 | Lampotang | |
| 2003/0033120 A1 | 2/2003 | Chiou | |

(Continued)

FOREIGN PATENT DOCUMENTS

DE    10310127    9/2004

(Continued)

OTHER PUBLICATIONS

Mu et al., "Multiple Fiducial Identification using the Hidden Markov Model in Image Guided Radiosurgery", 2006 IEEE.

(Continued)

*Primary Examiner* — Samir Ahmed
*Assistant Examiner* — Atiba Fitzpatrick
(74) *Attorney, Agent, or Firm* — Lowenstein Sandler PC

(57) ABSTRACT

A method and apparatus to develop an advanced correlation model of movement of a target within a patient, which needs less data points and can adapt to the changes of respiration behavior automatically.

24 Claims, 17 Drawing Sheets

U.S. PATENT DOCUMENTS

| | | | |
|---|---|---|---|
| 2003/0153823 A1* | 8/2003 | Geiser et al. .................. | 600/407 |
| 2004/0071337 A1 | 4/2004 | Jeung | |
| 2004/0092815 A1 | 5/2004 | Schweikard | |
| 2004/0158146 A1 | 8/2004 | Mate | |
| 2004/0254773 A1 | 12/2004 | Zhang et al. | |
| 2005/0033154 A1 | 2/2005 | deCharms | |
| 2005/0080332 A1 | 4/2005 | Shiu et al. | |
| 2006/0074299 A1 | 4/2006 | Sayeh | |
| 2006/0074304 A1 | 4/2006 | Sayeh | |
| 2007/0015991 A1 | 1/2007 | Fu | |
| 2007/0230765 A1 | 10/2007 | Wang et al. | |
| 2007/0244386 A1 | 10/2007 | Steckner et al. | |
| 2009/0110238 A1* | 4/2009 | Li et al. ......................... | 382/103 |

FOREIGN PATENT DOCUMENTS

| | | |
|---|---|---|
| WO | WO 99/27839 | 6/1999 |
| WO | WO03003796 | 1/2003 |
| WO | WO 2005/030330 A1 | 4/2005 |

OTHER PUBLICATIONS

Accuray Treatment Delivery Manual, Jan. 2007.

Coste-Maniere, E., "Robotic whole body stereotactic radiosurgery: clinical advantages of the CyberKnife® integrated system", The International Journal of Medical Robotics +Computer Assisted Surgery, 2005, www.roboticpublications.com, 14 pages.

Qin-Sheng Chen et al., "Fluoroscopic study of tumor motion due to breathing: Facilitating precise radiation therapy for lung cancer patients", Med. Phys. 28 (9), Sep. 2001, pp. 1850-1856.

Hiroki Shirato et al., "Intrafractional Tumor Motion: Lung and Liver", Seminars in Radiation Oncology, vol. 14, No. 1 (Jan.), 2004: pp. 10-18.

* cited by examiner

Path of Movement (2D)

Movement and Respiration vs. Time

Data Points on Path of Movement

Data Points on Time Scale

Linear Correlation Model

Multi-Poly Correlation of x-Movement
vs. Movement of External Marker

Multi-Poly Correlation of z-Movement
vs. Movement of External Marker

Multi-Poly Correlation Model

CONSTRAINED-CURVE CORRELATION MODEL

TECHNICAL FIELD

This invention relates to the field of radiation treatment and, in particular, to tracking target movement in radiation treatment.

BACKGROUND

Pathological anatomies such as tumors and lesions can be treated with an invasive procedure, such as surgery, but can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of X-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment), and hyperfractionation (e.g., 30 to 45 days of treatment). For convenience, the term "radiation treatment" is used herein to mean radiosurgery and/or radiotherapy unless otherwise noted.

In many medical applications, it is useful to accurately track the motion of a moving target in the human anatomy. For example, in radiosurgery, it is useful to accurately locate and track the motion of a target, due to respiratory and other patient motions during the treatment. Conventional methods and systems have been developed for performing tracking of a target treatment (e.g. radiosurgical treatment) on an internal target, while measuring and/or compensating for breathing and/or other motions of the patient. For example, U.S. Pat. Nos. 6,144,875 and 6,501,981, commonly owned by the assignee of the present application, describe such conventional systems. The SYNCHRONY® system, developed by Accuray, Inc., Sunnyvale, Calif., can carry out the methods and systems described in the above applications.

These conventional methods and systems correlate internal organ movement with respiration in a correlation model. The correlation model includes mappings of outside movement of an external marker to the internal tumor locations obtained through X-ray imaging. These conventional methods and systems correlate internal organ movement with respiration, using a linear model that is based on respiration position. However, these conventional technologies do not take into account internal organ movements along different inspiration and expiration paths. Although some internal organs may move along one path during inspiration and along another path during expiration, these conventional technologies do not distinguish these different paths because they consider only the position of the internal organ. In particular, conventional technologies use a linear approach to model the organ movement, despite the disparate inspiration and expiration paths of the internal organ. While the conventional linear modeling may have been an improvement over previous technologies, conventional linear modeling technologies are limited in their ability to model multi-path and other non-linear organ movements.

In addition, in setting up the correlation model before treatment, these conventional methods and systems rely on an operator to manually trigger the imaging system to acquire the image. It has been a challenge for operators to manually acquire multiple, evenly-distributed model points of the respiratory cycle for the correlation model. Manually triggering multiple images results in inconsistent distribution of model points of the respiratory cycle of the patient. Correlation models with evenly-distributed model points provide a more realistic model of the mappings of the outside movement of the external marker to the internal tumor locations. However, in some instances to overcome the uneven distribution of model points using the conventional methods and systems, the operator acquires additional images to get additional model points (e.g., images), resulting in an increase of unnecessary imaging occurrences.

BRIEF DESCRIPTION OF THE DRAWINGS

The present invention is illustrated by way of example, and not by way of limitation, in the figures of the accompanying drawings.

DETAILED DESCRIPTION

Figure 1:
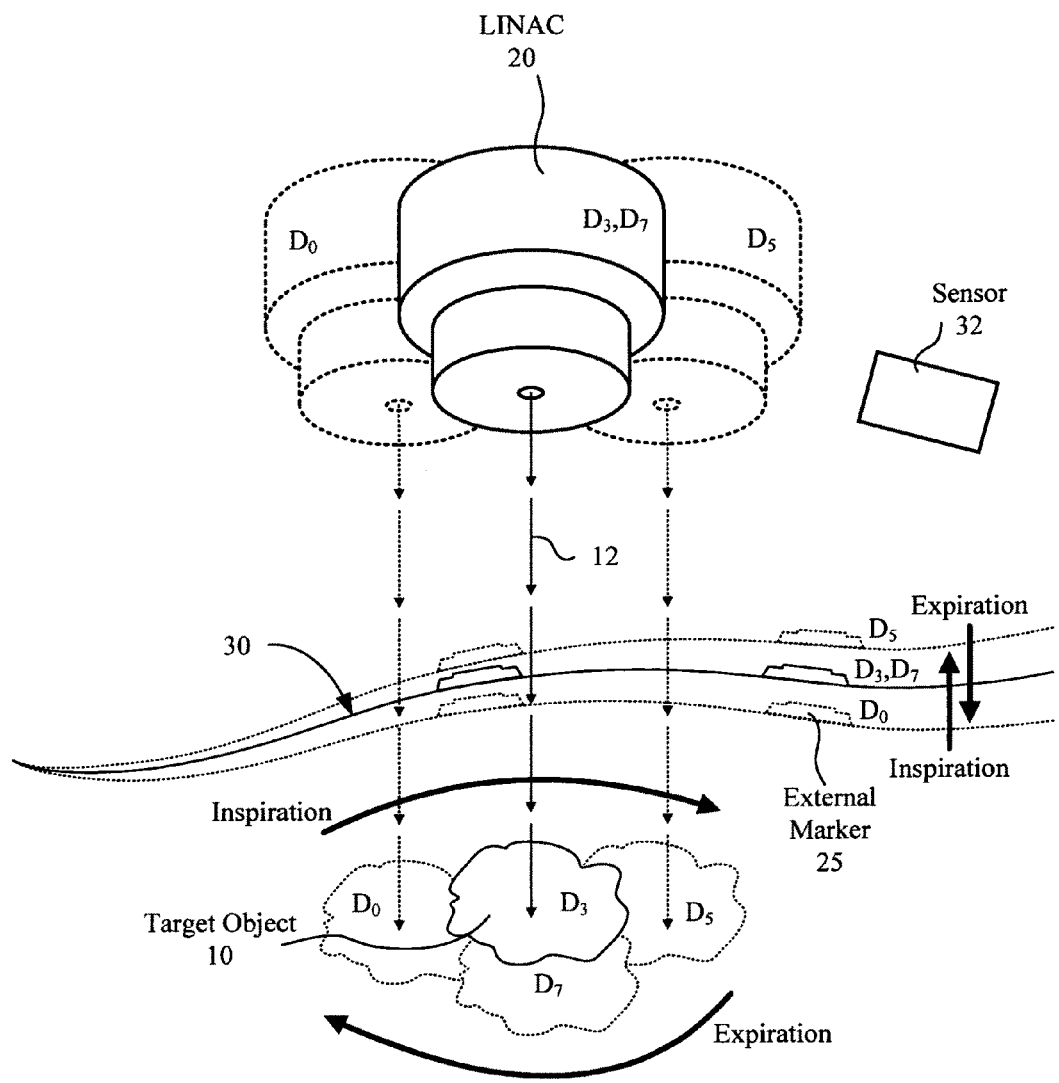
FIG. 1 illustrates a cross-sectional view of a treatment tracking environment.

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of the present invention include various operations, which will be described below. These operations may be performed by hardware components, software, firmware, or a combination thereof.

Certain embodiments may be implemented as a computer program product which may include instructions stored on a computer-readable medium. These instructions may be used to program a general-purpose or special-purpose processor to perform the described operations. A machine-readable medium includes any mechanism for storing information in a form (e.g., software, processing application) readable by a machine (e.g., a computer). The computer-readable medium may include, but is not limited to, magnetic storage media (e.g., floppy diskette); optical storage media (e.g., CD-ROM); magneto-optical storage media; read-only memory (ROM); random-access memory (RAM); erasable programmable memory (e.g., EPROM and EEPROM); flash memory; or another type of media suitable for storing electronic instructions.

Additionally, some embodiments may be practiced in distributed computing environments where the computer-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Embodiments of a method and system to identify a non-linear path of movement of a target based on multiple data points and an image using a parameterization function to approximate the non-linear path of movement. The parameterization function includes a constrained curve that intersects a principal axis of the plurality of data points at a first intersection and at a second intersection, and the constrained curve is tangent to the principal axis at the first and second intersections. As described above, a target within a patient may move due to respiratory motion, cardiac motions, or other patient motions. These patient motions may be periodic in nature. The periodic cycle of these motions can be measured by external sensors, such as a tracking sensor that tracks internal or external markers associated with a patient, a heart beat monitor, or the like. Historical data of previous periodic cycles, as measured by the external sensors, can be used in conjunction with one or more images to develop a correlation model that maps movement of the external marker to a target location of the target using the parameterization function. Since the parameterization function has only one unknown model parameter, only one sample model point (e.g., image) needs to be acquired to develop the correlation model. As such, the operator does not have to manually acquire multiple, evenly-distributed model points for the correlation model, resulting in non unnecessary imaging occurrences.

The embodiments described herein may include a parameterization function that satisfies four boundary conditions. A first boundary condition is that the constrained curve intersects the principal axis at the first intersection. A second boundary condition is that the constrained curve intersects the principal axis at the second intersection. A third boundary condition is that the constrained curve is tangent to the principal axis at the first intersection. The fourth boundary condition is that the constrained curve is tangent to the principal axis at the second intersection.

In one embodiment, a first sample point of the target location is determined using an acquired image. Using the parameterization function that satisfies the four boundary conditions and the first sample point, a shape of the constrained curve is determined. The first sample point defines an amount of curve of the constrained curve between the first and second intersections.

In one embodiment, the parameterization function is a fourth order polynomial that satisfies the four boundary conditions. In this embodiment, the first sample point is applied to the only unknown model parameter of the fourth order polynomial. In another embodiment, the parameterization function is a sinusoid function having a power of two or more that inherently satisfies the four boundary conditions. In this embodiment, the first sample point is applied to the only unknown model parameter of the sinusoid function.

In one embodiment, an inspiration interval and an expiration interval of the non-linear path of movement of the target are identified. The inspiration interval is associated with an approximate time during which the patient breathes in, and the expiration interval is associated with an approximate time during which the patient breathes out. The non-linear path of movement of the target includes an inspiration path associated with the inspiration interval, and an expiration path associated with the expiration interval. The multiple positions of the external marker, as measured by the external sensor, define an external path of movement of the external marker. The external path has a respiratory period associated with a respiratory cycle of the patient. In one embodiment, a derivative of the data points identifies whether the data point is part of the inspiration interval or the expiration interval. For example, the derivative may include a directional indicator that can be used to identify whether the model point is part of the inspiration interval or the expiration interval.

In one embodiment, the correlation model is a dual-constrained-curve model. The dual-constrained-curve correlation model includes a first constrained curve associated with the non-linear path of movement of the target over the inspiration period, and a second constrained curve associated with the non-linear path of movement of the target over the expiration period. The correlation model can then be used to derive a target position of the target.

In another embodiment, the target locating system includes a shrinking algorithm to adapt the correlation model. The shrinking algorithm is configured to automatically adapt the original correlation model to the changes in the movements. In one embodiment, a change in magnitude of movement of the external marker is detected, and in response, the correlation model is automatically scaled to more accurately track the movement of the target.

The embodiments described herein may be implemented in already existing target locating systems with minimal impact to the preexisting architecture, or alternatively, in newly developed target locating systems.

As described above, a correlation model is developed to correlate internal organ movement with respiration. The correlation model includes mappings of one or more external markers to the internal target position (e.g., tumor location) obtained through real-time X-ray imaging. The embodiments described herein, however, create the correlation model using one or more acquired images as model points and the parameterization function that satisfies the four boundary conditions. Although some of the embodiments described below are directed to developing a correlation model with model points in a breathing waveform (e.g., respiratory cycle) to track movement of the target based on a patient's breathing, in other embodiments, the correlation model can be developed for other types of waveforms, such as heartbeat cycles of a patient, or other waveforms of other periodic motions of the patient.

In one embodiment, a method and system are presented to identify the correlation between movement(s) of a target, such as an internal organ, and respiration (or other motion such as heartbeat) of a patient. These movements may include linear movements, non-linear movements, and asymmetric movements. In one embodiment, the method and system may facilitate modeling movement paths of a target that moves along different paths during inspiration and expiration, respectively. In one embodiment, generating the correlation model includes acquiring data points representative of positions over time of an external marker associated with the patient. In one embodiment, the external marker defines an external path of movement of the external marker during the respiratory cycle of the patient. The data points correspond to the pretreatment images. The method and system identifies a path of movement of the target based on the data points and at least one pretreatment image, and develops the correlation model using the parameterization function to approximate the path of movement of the target.

The method and system may consider position, speed, and/or direction of respiration or the internal object to develop one or more correlation models. The method and system also may use data points in time for which the position of the target is known. Respiration may be monitored in parallel with the monitoring of the target position. Information about the position and the speed/direction of respiration may be obtained at the time of interest. Once established, a correlation model may be used along with a respiration monitoring system to locate and track the internal movement of a target, such as an organ, region, lesion, tumor, and so forth.

FIG. 1 illustrates a cross-sectional view of a treatment tracking environment. The treatment tracking environment depicts corresponding movements of an internal target 10 within a patient, a linear accelerator (LINAC) 20, and an external marker 25. The illustrated treatment tracking environment is representative of a patient chest region, for example, or another region of a patient in which an internal organ might move during the respiratory cycle of the patient. In general, the respiratory cycle of a patient will be described in terms of an inspiration interval and an expiration interval, although other designations and/or delineations may be used to describe a respiratory cycle.

In one embodiment, the LINAC 20 moves in one or more dimensions to position and orient itself to deliver a radiation beam 12 to the target 10. Although substantially parallel radiation beams 12 are depicted, the LINAC 20 may move around the patient in multiple dimensions to project radiation beams 12 from several different locations and angles. The LINAC 20 tracks the movement of the target 10 as the patient breathes, for example. One or more external markers 25 are secured to, or otherwise disposed on, the exterior 30 of the patient in order to monitor the patient's breathing cycle. In one embodiment, the external marker 25 may be a device such as a light source (e.g., light emitting diode (LED)) or a metal button attached to a vest worn by the patient. Alternatively, the external marker 25 may be attached to the patient's clothes or skin in another manner.

As the patient breathes, a tracking sensor 32 tracks the location of the external marker 25. For example, the tracking sensor may track upward movement of the external marker 25 during the inspiration interval and downward movement of the external marker 25 during the expiration interval. The relative position of the external marker 25 is correlated with the location of the target 10, as described below, so that the LINAC 20 may move relative to the location of the external marker 25 and the correlated location of the target 10. In another embodiment, other types of external or internal markers may be used instead of, or in addition to, the illustrated external marker 25.

As one example, the depicted target 10 is shown in four positions, designated as $D_0$, $D_3$, $D_5$, and $D_7$. The first position, $D_0$, may correspond to approximately the beginning of the inspiration interval. The second position, $D_3$, may correspond to a time during the inspiration interval. The third position, $D_5$, may correspond to approximately the end of the inspiration interval and the beginning of the expiration interval. The fourth position, $D_7$, may correspond to a time during the expiration interval. Additional positions of the target 10 on the path of movement are graphically shown and described in more detail with reference to the following figures. As the patient breathes, the target 10 may move along a path within the patient's body. In one embodiment, the path of the target 10 is asymmetric in that the target 10 travels along different paths during the inspiration and expiration intervals. In another embodiment, the path of the target 10 is at least partially non-linear. The path of the target 10 may be influenced by the size and shape of the target 10, organs and tissues surrounding the target 10, the depth or shallowness of the patient's breathing, and so forth.

Similarly, the external marker 25 is shown in a first position, $D_0$, a second position, $D_3$, a third position, $D_5$, and a fourth position, $D_7$, which correspond to the positions of the target 10. By correlating the positions of the external marker 25 to the target 10, the position of the target 10 may be derived from the position of the external marker 25 even though the external marker 25 may travel in a direction or along a path that is substantially different from the path and direction of the target 10. The LINAC 20 is also shown in a first position, $D_0$, a second position, $D_3$, a third position, $D_5$, and a fourth position, $D_7$, which also correspond to the positions of the target 10. In this way, the movements of the LINAC 20 may be substantially synchronized to the movements of the target 10 as the position of the target 10 is correlated to the sensed position of the external marker 25.

Figure 2:
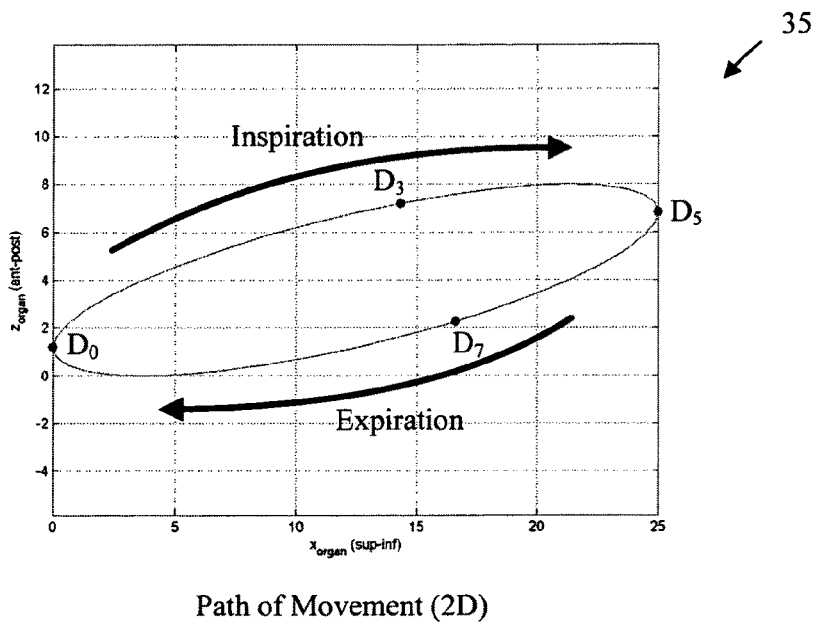
FIG. 2 is a graphical representation of an exemplary two-dimensional path of movement of an internal target during a respiration period.

FIG. 2 is a graphical representation 35 of an exemplary two-dimensional path of movement of an internal target 10 during a respiration period. The horizontal axis represents displacement (e.g., in millimeters) of the target 10 in a first dimension (x). The vertical axis represents displacement (e.g., in millimeters) of the target 10 in a second dimension (z). The target 10 may similarly move in a third dimension (y). As shown in the graph 35, the path of movement of the target 10 is non-linear. Additionally, the path of movement is different during an inspiration period and an expiration period. As an example, the inspiration path may correspond to the upper portion of the graph 35 between zero and twenty-five in the x direction, with zero being a starting reference position, $D_0$, and twenty-five being the maximum displacement position, $D_5$, at the moment between inspiration and expiration. The corresponding expiration period may be the lower portion of the graph 35 between $D_5$ and $D_0$. In the depicted embodiment, the displacement position $D_3$ is on the inspiration path roughly between $D_0$ and $D_5$. Similarly, the displacement position $D_7$ is on the expiration path roughly between $D_5$ and $D_0$. These displacement points are shown with additional displacement points in FIG. 4.

Figure 3:
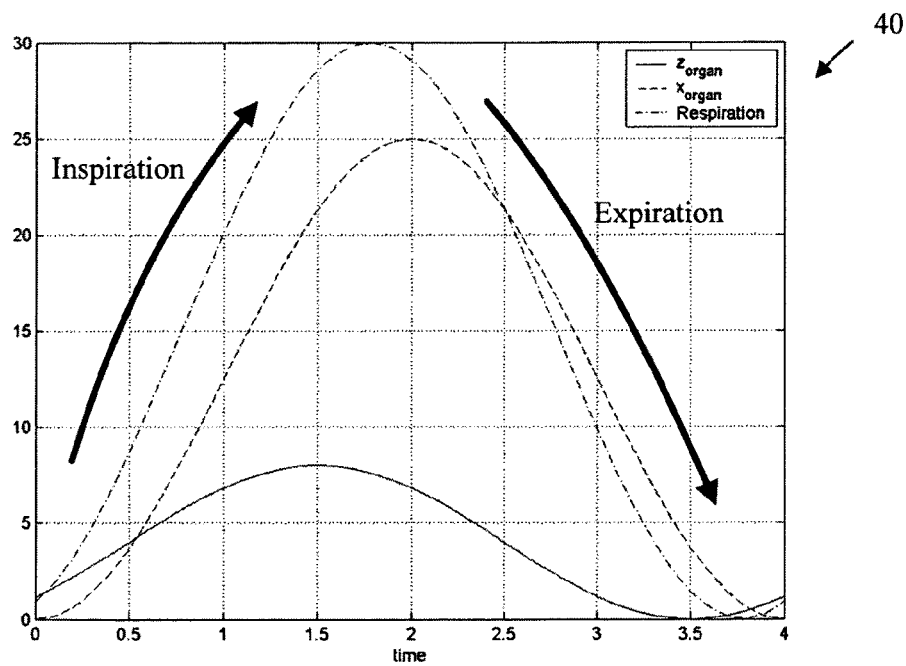
FIG. 3 is a graphical representation of an exemplary path of movement of an internal target during a respiration period, as a function of time.

FIG. 3 is a graphical representation 40 of an exemplary path of movement of an internal target 10 during a respiration period, as a function of time. The graph 40 shows the displacement (e.g., in millimeters) of the target 10 over time (e.g., in seconds) in the x direction (dashed line) and in the z direction (solid line). The graph 40 also shows the displacement (in millimeters) of, for example, an external marker 25 to identify the respiration period (dashed line). In the depicted embodiment, the external marker 25 is maximally displaced (approximately 30 mm) more than the target 10 in the x direction (approximately 25 mm) or in the z direction (approximately 8 mm). However, the maximum displacement of the target 10 in the various directions does not necessarily align with the maximum displacement of the external marker 25 associated with the respiratory cycle. Additionally, the maximum displacement of the target 10 in the one direction does not necessarily align with the maximum displacement in another direction. For example, the maximum displacement of the external marker 25 occur at approximately 1.75 s, while the maximum displacement of the internal organ 10 in the x and z directions may occur at approximately 2.0 and 1.5 seconds, respectively. These misalignments may be present in both the inspiration and expiration paths.

Figure 4:
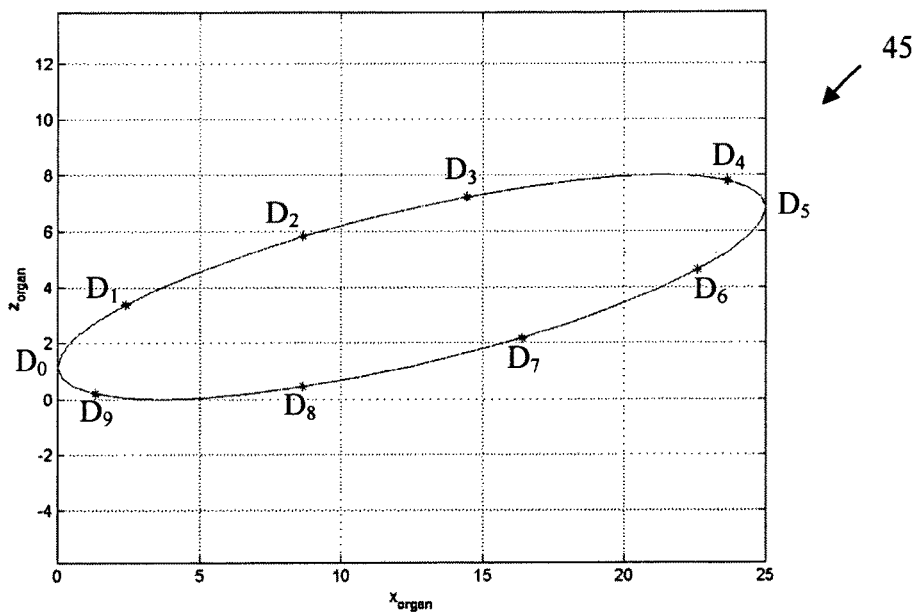
FIG. 4 is a graphical representation of an exemplary set of data points associated with the path of movement shown in FIG. 2.

FIG. 4 is a graphical representation 45 of an exemplary set of data points $D_0$-$D_9$ associated with the path of movement shown in FIG. 2. In particular, the data points $D_0$-$D_9$ are superimposed on the path of movement of the target 10. The data points $D_0$-$D_9$ correspond to various points in time during the respiration period. In the illustrated embodiment, one data point data point $D_0$ designates the initial reference location of the target 10 prior to the inspiration interval. Four data points $D_1$-$D_4$ designate the movement of the target 10 during the inspiration interval. The data point $D_5$ designates the moment between the inspiration and expiration intervals. The data points $D_6$-$D_g$ designate the movement of the target 10 during the expiration interval. The following table provides approximate coordinates for each of the data points $D_0$-$D_9$. Similar coordinates may be provided for the displacement of the external marker 25 or the displacement of the target 10 in another direction.

TABLE 1

Data Point Coordinates.

| Data Point | (x, z) (mm) |
| --- | --- |
| $D_0$ | (0, 1) |
| $D_1$ | (2, 3) |
| $D_2$ | (8, 5) |
| $D_3$ | (14, 7) |
| $D_4$ | (24, 8) |
| $D_5$ | (25, 7) |
| $D_6$ | (23, 5) |
| $D_7$ | (16, 2) |
| $D_8$ | (8, 0) |
| $D_9$ | (1, 0) |

Figure 5:
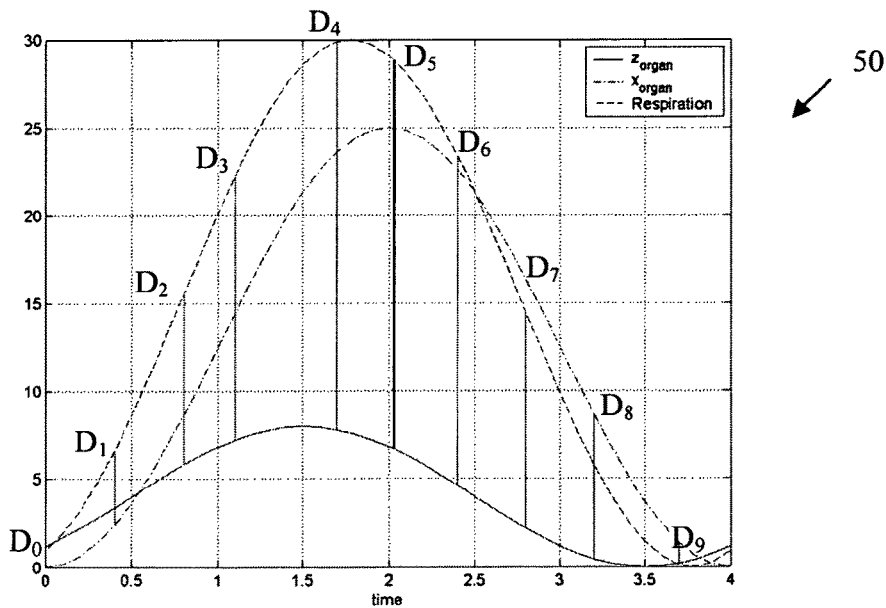
FIG. 5 is a graphical representation of an exemplary set of data points associated with the path of movement shown in FIG. 3.

FIG. 5 is a graphical representation 50 of the exemplary set of data points $D_0$-$D_9$ associated with the paths of movement shown in FIG. 3. The data points $D_0$-$D_9$ are represented by vertical lines superimposed on the path of movement of the target 10 and the external marker 25. The following table provides approximate times corresponding to each of the data points $D_0$-$D_9$, as well as approximate displacement values, r, for the external marker 25.

TABLE 2

Data Point Times.

| Data Point | Time (s) | r (mm) |
| --- | --- | --- |
| $D_0$ | 0.0 | 1 |
| $D_1$ | 0.4 | 6 |
| $D_2$ | 0.8 | 16 |
| $D_3$ | 1.1 | 22 |
| $D_4$ | 17 | 30 |
| $D_5$ | 2.4 | 28 |
| $D_6$ | 2.8 | 23 |
| $D_7$ | 3.2 | 14 |
| $D_8$ | 3.7 | 5 |
| $D_9$ | 4.0 | 0 |

Figure 6A:
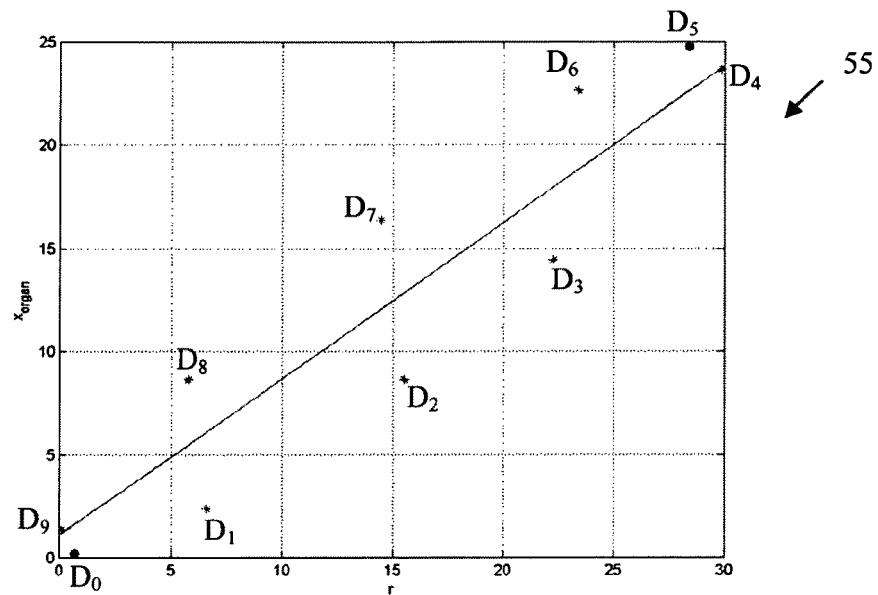
FIG. 6A is a graphical representation of an exemplary least square fit linear correlation model of the path of movement in a first dimension, as a function of movement of an external marker.

FIG. 6A is a graphical representation 55 of an exemplary least square fit linear correlation model of the path of movement in a first dimension, as a function of the displacement, r, of an external marker 25. In particular, the graph 55 shows the (r,x) coordinates from the data points $D_0$-$D_9$ above and superimposes a linear correlation model (dashed line). The following table provides approximate (r,x) coordinates corresponding to each of the data points $D_0$-$D_9$.

TABLE 3

Data Point Coordinates.

| Data Point | (r, x) (mm) |
|---|---|
| $D_0$ | (1, 0) |
| $D_1$ | (6, 2) |
| $D_2$ | (16, 8) |
| $D_3$ | (22, 14) |
| $D_4$ | (30, 24) |
| $D_5$ | (28, 25) |
| $D_6$ | (23, 23) |
| $D_7$ | (14, 16) |
| $D_8$ | (5, 8) |
| $D_9$ | (0, 1) |

The linear correlation model may be used to estimate the x displacement of the target 10 based on the respiration displacement, r, measured by the external marker 25. The following equation is exemplary of a linear correlation model that may be employed in conventional linear modeling systems:

$$\begin{Bmatrix} x_{organ} \\ y_{organ} \\ z_{organ} \end{Bmatrix} = \begin{Bmatrix} A_x \\ A_y \\ A_z \end{Bmatrix} r + \begin{Bmatrix} B_x \\ B_y \\ B_z \end{Bmatrix} \quad (1)$$

which may be written in a more compact form as follows:

$$x = ar + b \quad (2)$$

Figure 6B:
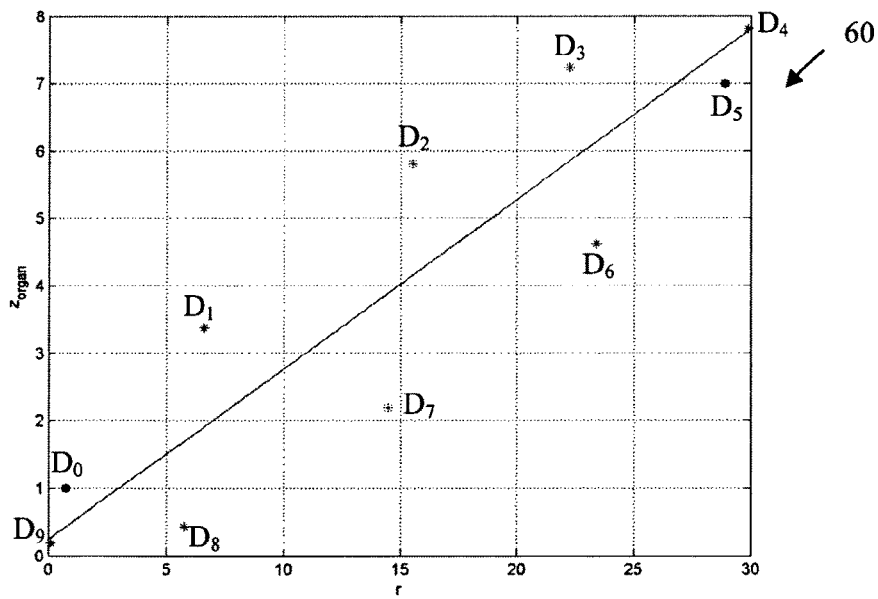
FIG. 6B is graphical representation of an exemplary least square fit linear correlation model of the path of movement in a second dimension, as a function of movement of an external marker.

FIG. 6B is a graphical representation 60 of an exemplary least square fit linear correlation model of the path of movement in a second dimension, as a function of the displacement, r, of an external marker 25. In particular, the graph 60 shows the (r,z) coordinates from the data points $D_0$-$D_9$ above and superimposes a linear correlation model (dashed line). The following table provides approximate (r,z) coordinates corresponding to each of the data points $D_0$-$D_9$. The linear correlation model may be used to estimate the z displacement of the target 10 based on the respiration displacement, r, measured by the external marker 25.

TABLE 4

Data Point Coordinates.

| Data Point | (r, z) (mm) |
|---|---|
| $D_0$ | (1, 1) |
| $D_1$ | (6, 3) |
| $D_2$ | (16, 5) |
| $D_3$ | (22, 7) |
| $D_4$ | (30, 8) |
| $D_5$ | (28, 7) |
| $D_6$ | (23, 5) |
| $D_7$ | (14, 2) |
| $D_8$ | (5, 0) |
| $D_9$ | (0, 0) |

Figure 6C:
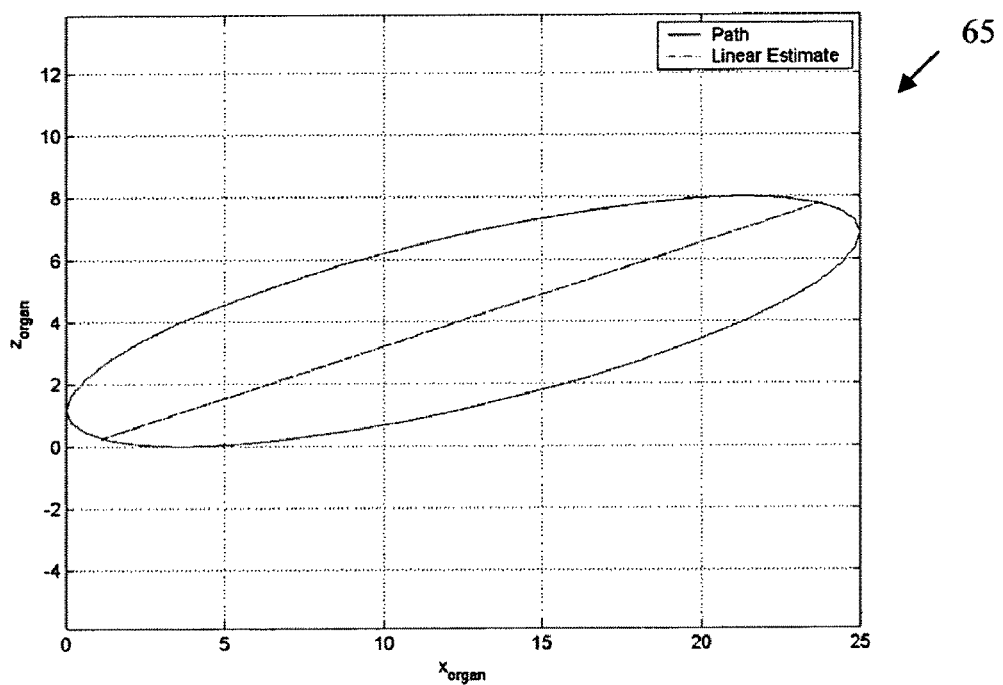
FIG. 6C is a graphical representation of an exemplary estimated path for a linear correlation model in two dimensions.

FIG. 6C is a graphical representation 65 of an exemplary estimated path for a linear correlation model. The graph 65 superimposes the linear correlation model for the x and z directions on the path of movement, shown in FIG. 2, of the target 10. While the linear correlation model is fairly accurate at about (x,z)=(2,0) and (x,z)=(23,8), the linear correlation model has relatively large estimation errors for all of the other coordinates along the path of movement. The estimation error corresponding to the x direction may be determined by the vertical difference (e.g., in millimeters) between the linear correlation model and either the inspiration path (e.g., upper portion) or the expiration path (e.g., lower portion). Similarly, the estimation error for the z direction may be determined by the horizontal difference (e.g., in millimeters) between the linear correlation model and either the inspiration path (e.g., upper portion) or the expiration path (e.g., lower portion).

Figure 7A:
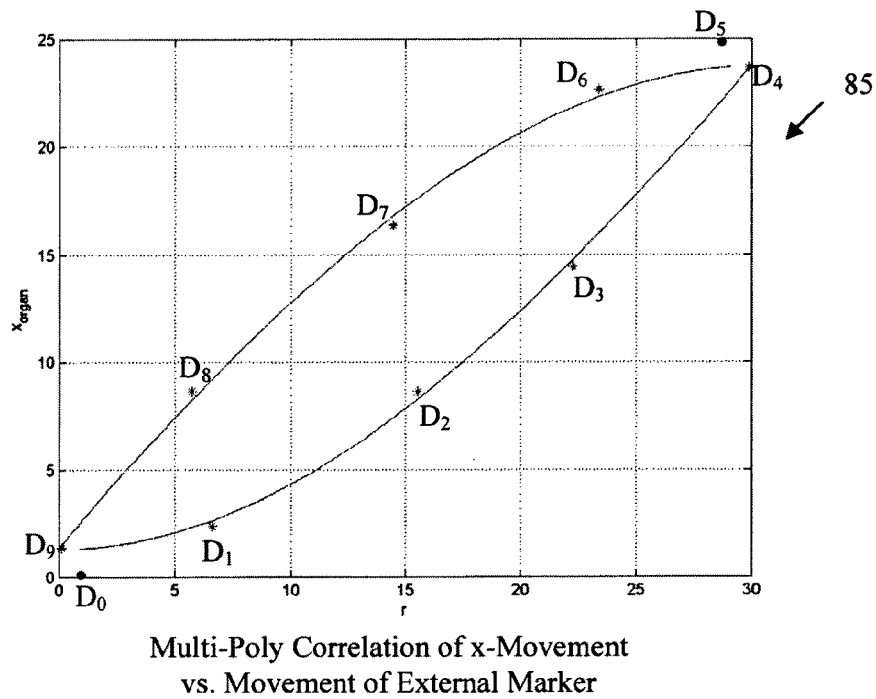
FIG. 7A is a graphical representation of an exemplary multi-poly correlation model of the path of movement in a first dimension, as a function of movement of an external marker.

FIG. 7A is a graphical representation 85 of an exemplary multi-poly correlation model of the path of movement in a first dimension, as a function of the displacement, r, of an external marker 25. In particular, the graph 85 shows the (r,x) coordinates from the data points $D_0$-$D_9$ above and superimposes a multi-poly correlation model (dashed line). The multi-poly correlation model also may be referred to herein as a curvilinear correlation model or, more generally, a nonlinear correlation model. The approximate (r,x) coordinates corresponding to each of the data points $D_0$-$D_9$ is provided in Table 3 above.

The nonlinear correlation model may be used to estimate the x displacement of the target 10 based on the respiration displacement, r, measured by the external marker 25. The following equation is exemplary of a nonlinear correlation model:

$$x = f(r) \quad (3)$$

where f(r) describes the curve and may be selected depending on the shape of the path of movement of the target 10. In a more particular embodiment, a third order polynomial may be selected as an example of the vector function f(r) of the equation above. In one embodiment, the resulting polynomial curve may be described according to the following equation:

$$x = \sum_{n=0}^{3} a_n r^n \quad (4)$$

In another embodiment, the speed of the respiratory motion (i.e., the derivative of the respiration displacement, r) may be used to build a nonlinear correlation model, as illustrated, that more closely approximates the organ path. For example, using the speed of the external marker 25 may be useful in cases in which the target 10 takes different paths during the inspiration and expiration intervals, respectively, of the respiration period. In other embodiments, the displacement and/or speed of other motions, other than respiration, may be used in addition to or instead of the respiration. One example of an equation that takes into account both displacement, r, and speed, $\dot{r}$, as a second independent variable, is as follows:

$$x = f(r, \dot{r}) \quad (5)$$

The multi-poly correlation model may be used to estimate the x displacement of the target 10 based on the speed, $\dot{r}$, and the direction of motion (i.e., the positive or negative sign of $\dot{r}$) of the external marker 25. In one embodiment, the directional indicators may be used to split the path of movement of the target 10 into two separate curvilinear paths. The directional indicators also may be used to distinguish the data points $D_1$-$D_4$ corresponding to the inspiration interval from the data points $D_6$-$D_9$ corresponding to the expiration interval. In another embodiment, this approach may be implemented in with a third order polynomial, as described above, and the multi-poly correlation model may be described by the following equation:

$$x = \begin{cases} \sum_{n=0}^{3} a_n^+ r^n & \dot{r} \geq 0 \\ \sum_{n=0}^{3} a_n^- r^n & \dot{r} < 0 \end{cases} \quad (6)$$

In one embodiment, the foregoing equation essentially separates the data points into two separate groups according to their respective direction of motion of each data point. In particular, data points whose direction is positive (according to a predetermined sign convention) may be placed in a first data set and data points whose direction is negative may be placed in a second data set. The data sets may correspond to the inspiration and expiration intervals. However, in another embodiment, the data sets for each of the polynomial approximations may overlap. For example, data points that have a relatively small directional value may be placed in more than one data set, regardless of sign. As an example, the data points $D_0$, $D_4$, $D_5$, and $D_9$ may be placed in each of two data sets. Accordingly, the foregoing equations may be modified to account for these overlapping data sets. The outputs of multiple polynomials may be averaged for the data points that belong to more than one data set. In another embodiment, more than two polynomial approximations may be used to approximate the movement of the target 10.

Figure 7B:
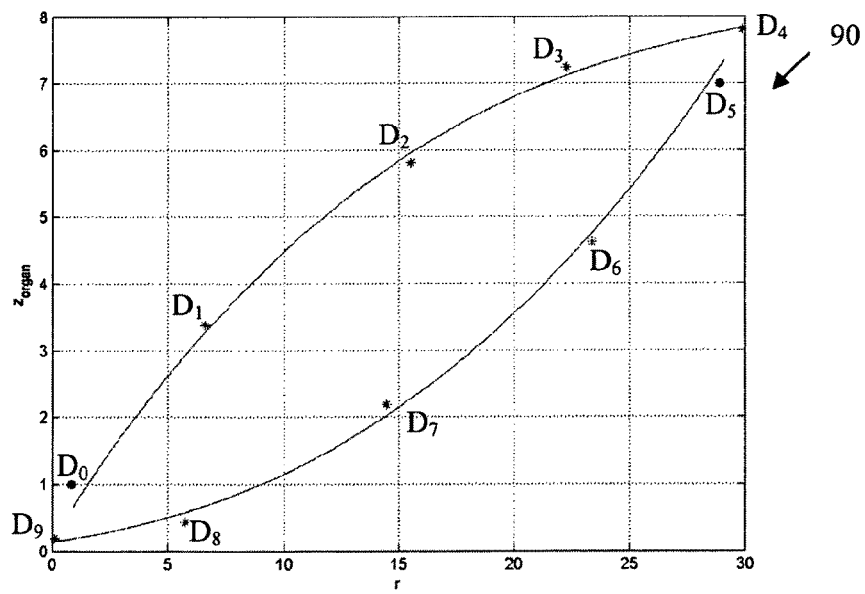
FIG. 7B is a graphical representation of an exemplary multi-poly correlation model of the path of movement in a second dimension, as a function of movement of an external marker.

FIG. 7B is a graphical representation 90 of an exemplary multi-poly correlation model of the path of movement in a second dimension, as a function of the displacement, r, of an external marker 25. In particular, the graph 90 shows the (r,z) coordinates from the data points $D_0$-$D_9$ above and superimposes a multi-poly correlation model (dashed line). The approximate (r,z) coordinates corresponding to each of the data points $D_0$-$D_9$ are provided in Table 4 above.

Figure 7C:
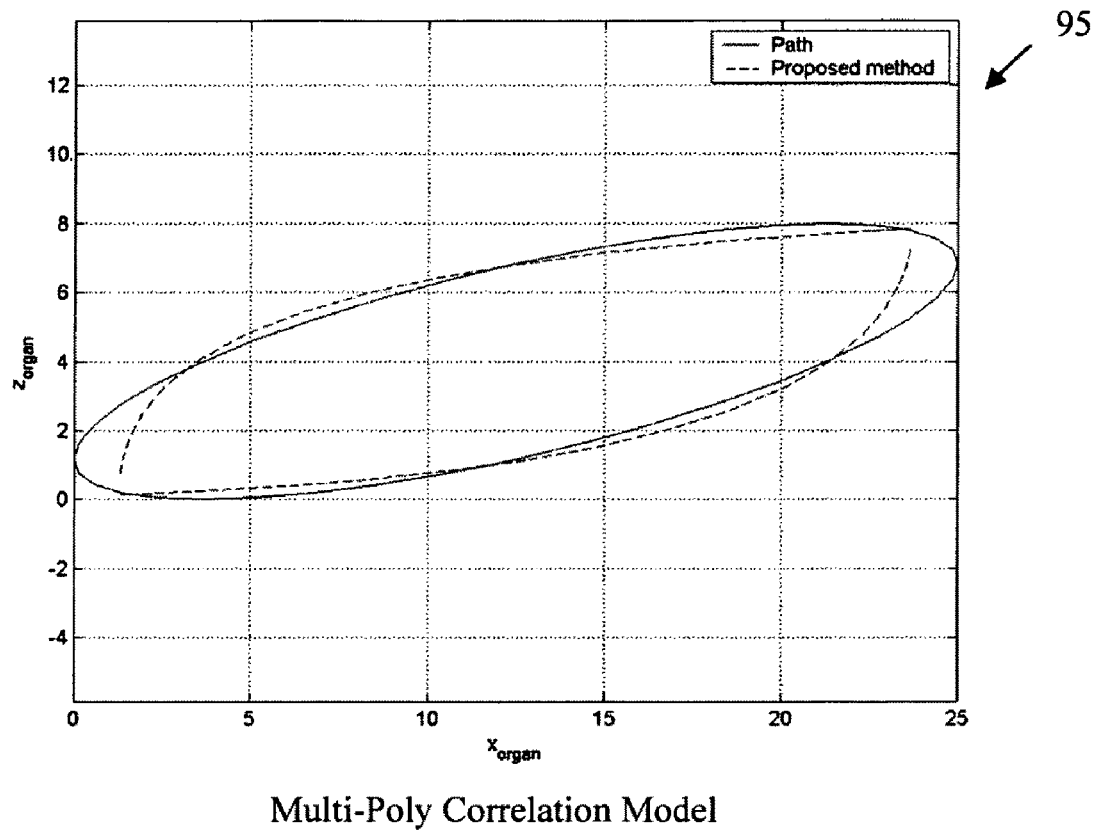
FIG. 7C is a graphical representation of an exemplary estimated path for a multi-poly correlation model.

FIG. 7C is a graphical representation 95 of an exemplary estimated path for a multi-poly correlation model. The graph 95 superimposes the multi-poly correlation model for the x and z directions on the path of movement, shown in FIG. 2, of the target 10. In comparison to the linear correlation model and third order nonlinear correlation model described above, the multi-poly correlation model is much more accurate for most, if not all, of the coordinates along the path of movement of the target 10.

The illustrated multi-poly correlation model includes two polynomial approximations. However, other embodiments may include more than two polynomial approximations. In another embodiment, the multi-poly correlation model also may include one or more linear approximations to approximate a portion of the path of movement.

The dual curvilinear model illustrated in FIG. 7C, however, may have some problems. For example, in the dual curvilinear model there is an inspiration polynomial approximation and an expiration polynomial approximation. However, the dual curvilinear model has problems when approximating the target locations at the regions (also referred to as boundary regions) corresponding to the moments between the inspiration and expiration periods (near x=0 and x=25). Approximating the target location at these regions is referred to as modeling the boundary condition. Using the dual curvilinear model, the boundary condition is not easy to fulfill. For example, in order to approximate the target location in these regions, methods may be implemented to link the inspiration polynomial approximation and the expiration polynomial approximation. Linking the approximations may be referred to as blending or matching approximations. The matching approximations may include polynomial approximations, linear approximations, or a combination thereof to blend the inspiration and expiration approximations. Although even using matching approximations, the matching approximations may result in transitions at the boundary conditions that have a faster rate of change than the rate of change of the portions of the inspiration and expiration approximations that are not at the boundary conditions, resulting in non-optimal tracking motion (e.g., robot motion of the LINAC as described below).

Another problem with the dual curvilinear model is the number of unknown model parameters. In order to define multiple unknown model parameters multiple data points need to be obtained. For example, when the model only has one unknown model parameter, one image may be acquired to determine one sample point to define the one unknown model parameter. However, when there is more than one unknown model parameter, additional images are needed to determine multiple sample points to define the one or more unknown model parameters. This may result in an increase of unnecessary imaging occurrences. In one example of a dual curvilinear model that uses the following second order polynomial, there are three unknown model parameters, a, b, and c for each side.

$$x = ar^2 + br + c \quad (7)$$

In this example, at least three model points (e.g., images) are needed to determine the three unknown model parameters, a, b, and c for each side. Therefore, in this example, at least six model points (e.g., images) are needed to determine the total six unknown model parameters (a, b, and c for both sides). However, these model points need to be evenly distributed. The model points represent, for example, the different phases in a respiratory cycle.

Figure 8A:
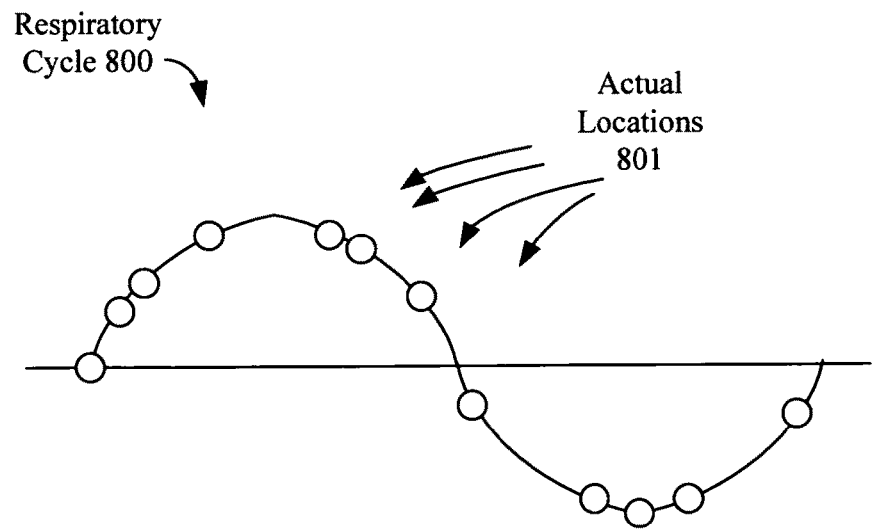
FIG. 8A is a graphical representation of exemplary unevenly-distributed model points of a respiratory cycle using a conventional manual timing process in developing a dual curvilinear model that uses a second order polynomial.

FIG. 8A is a graphical representation of exemplary unevenly-distributed model points of a respiratory cycle 800 using a conventional manual timing process in developing a dual curvilinear model that uses a second order polynomial. The respiratory cycle 800 includes multiple model points at the actual locations 801. The model points at the actual locations 801 represent the location in the respiratory cycle 800 at which the images were actually acquired using the manual timing process. Since the timing of the image acquisitions is manually controlled, the distribution of model points is not evenly distributed over the respiratory cycle 800. As described above, in order to determine the total six unknown model parameters (three unknown model parameters for each side), at least six model points are needed, however, since the model points are not evenly distributed, additional model points are acquired in an attempt to obtain model points at designated phases of the respiratory cycle to develop a more accurate correlation model. Also, it should be noted that in this example, more than six model points are added to the model data set, resulting in an increase of unnecessary imaging occurrences.

Another problem with the dual curvilinear model is that the dual curvilinear model is hard to adapt when a significant change in respiration behavior is detected. For example, during the treatment of a patient, the patient's respiration behavior may change significantly such that the accuracy of the curvilinear model is decreased.

Figure 8B:
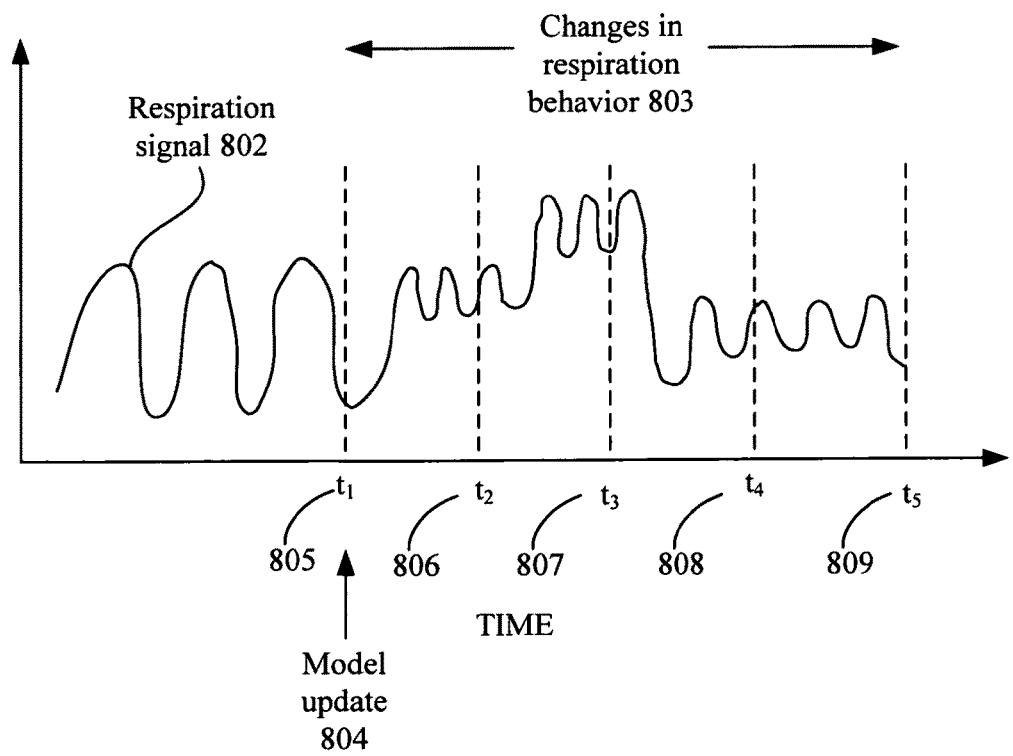
FIG. 8B is a graphical representation of an exemplary respiration signal over time representative of changes in respiration behavior.

FIG. 8B is a graphical representation of an exemplary respiration signal 802 over time representative of changes in respiration behavior. Before time $t_1$ 805, the respiration signal 802 is representative of a first respiration behavior. For example, the respiration signal 802 in the first respiration behavior may have certain characteristics, such as a certain magnitude and/or frequency. At the time $t_1$ 805, the correlation model is updated (e.g., model update 804) to approximate the target location based on the first respiration behavior. Between times $t_1$ 805 and $t_5$ 809, there is no model update. In this example, the correlation model is based on a dual curvilinear model as described above. Using the dual curvilinear model, the approximation of the target location performs well when the respiration signal 802 behaves according to the first respiration behavior; however, the dual curvilinear model performs poorly when there is a significant change in the respiration behavior, such as illustrated in FIG. 8B as the changes in respiration behavior 803. The changes in respiration behavior 803 may have different characteristics than the first respiration behavior, such as different magnitudes, different frequency, or the like. For example, the respiration signal 802 during times $t_1$ 805 and $t_5$ 809 has a smaller magnitude of displacement than the respiration signal 802 before the time $t_1$ 805. As a result, the model output will be incorrect when there is a change in respiration behavior. For example, at time $t_4$ 808 the model output will be a higher value than it should be, since the magnitude of the displacement at the time $t_4$ 808 is smaller in magnitude than the correlation model, which is based on the magnitude of displacement of the first respiration behavior. Also, the change in respiration behavior 803 may cause the model output to be discontinuous. For example, the model output may jump from the inspiration approximation curve to the expiration approximation curve in a discontinuous manner, as illustrated in FIG. 8C.

Figure 8C:
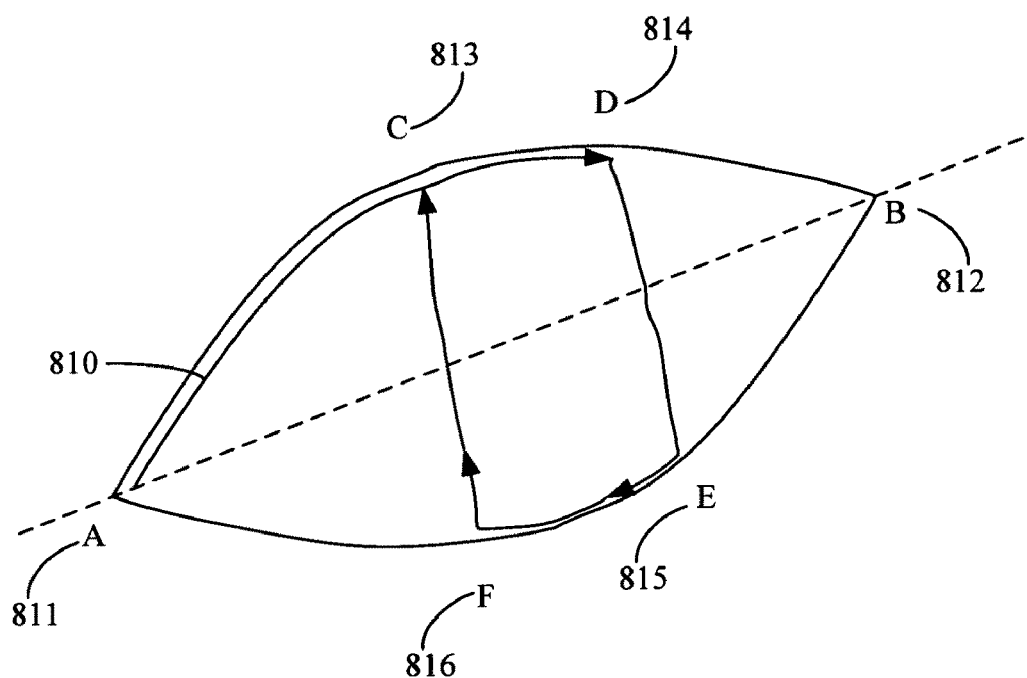
FIG. 8C is a graphical representation of an exemplary estimated path for a multi-poly correlation model when there is the change in respiration behavior of FIG. 8B.

As illustrated in FIG. 8C, as the respiration signal 802 follows the first respiration behavior, the correlation model provides model output that is continuous along the curve from point A 811 to point B 812 and from the point B 812 back to the point A 811 in a continuous manner. However, as the respiration signal 802 changes from the first respiratory behavior, instead of providing model output that is continuous along the curve from point A 811 to point B 812 and from point B 812 to point A 811, the model output 810 jumps from the one curve to another in a discontinuous manner, for example, between point D 814 and point E 815 and between point F 816 and point C 813. The discontinuity in model output can cause non-optimal motion of the LINAC 20. As described above, the motion of the LINAC 20 can be synchronized to the movements of the target 10, and as such, discontinuity in the model output can disturb the expected continuous motion of the LINAC 20. For example, the LINAC 20 may jerk, accelerate, decelerate, jolt, or the like, in response to synchronizing its motion to the discontinuous model output.

In order to overcome the problems described above, in one embodiment, a constrained-curve correlation model may be used to approximate the target location. The constrained-curve correlation model is a correlation model that maps movement of the external marker 25 to a target location of the target 10 using a parameterization function to approximate a non-linear path of movement. One or more parameterization functions of the correlation model can be used to generate one or more constrained curves. The correlation model may include two constrained curves, for example, one for the inspiration approximation and another for the expiration approximation. Each of the constrained curves intersects a principal axis of data points of the external marker 25 at a first intersection and at a second intersection, and each of the constrained curves is tangent to the principal axis at the first and second intersections. The principal axis may be determined using a linear approximation of the data points of the external marker 25. The linear approximation may be done using a linear square fit or other known linear fits.

Each constrained curve includes four boundary conditions. The first boundary condition is that the constrained curve intersects the principal axis at the first intersection. The second boundary condition is that the constrained curve intersects the principal axis at the second intersection. The third boundary condition is that the constrained curve is tangent to the principal axis at the first intersection. The fourth boundary condition is that the constrained curve is tangent to the principal axis at the second intersection.

By using the constrained curve that satisfies these four boundary conditions, the correlation model does not have problems that the dual curvilinear model has when approximating the target locations at the boundary regions corresponding to the moments between the inspiration and expiration periods (e.g., near x=0 and x=25 of FIG. 7C). By using a constrained curve that satisfies these four boundary conditions, the shape of the curves at the boundary regions is already determined as part of the correlation model. Also, by using a constrained curve that satisfies these four boundary conditions, no matching approximations or blending is required to link the inspiration and expiration approximations.

In one embodiment, the parameterization function is used to identify a non-linear path of movement of the target based on the data points of the external marker 25 and at least one image (e.g., model point). In one embodiment, the parameterization function includes only one model parameter. For example, in one embodiment, the parameterization function is a fourth order polynomial as set forth in the following equation:

$$x = a\rho^4 + b\rho^3 + c\rho^2 + d\rho + e \qquad (8)$$

where a, b, c, d, e are unknown model parameters and $\rho$ is a displacement of the target location. However, by applying the four boundary conditions to the fourth order polynomial, the fourth order polynomial may be simplified as set forth in the following equation:

$$x = a\rho^4 - 2a\rho^3 + a\rho^2 \qquad (9)$$

where a is the only unknown model parameter and $\rho$ is the displacement of the target location. Since the simplified fourth order polynomial expressed in Eq. (9) only includes one unknown model parameter, only one model point (e.g., image) needs to be obtained to be applied to the simplified equation to determine the unknown model parameter, a. Alternatively, more than one model points may be obtained.

It should also be noted that for a second order polynomial, there are only three unknown model parameters and for a fourth order polynomial, there are five unknown model parameters. However, by applying the four boundary conditions, as described herein, the fourth order polynomial includes only one unknown model parameter, which reduces the number of images needed to develop the correlation model, as compared to a correlation model that uses a second order polynomial to approximate the target location. Similarly, there is only one unknown model parameter for other parameterization functions that implicitly satisfies the four boundary conditions. As described above, six model points need to be obtained to develop a correlation model using the dual second order polynomial. However, in the embodiments described herein, less than six model points can be obtained to develop the correlation model. In another embodiment, only one model point is obtained to develop the correlation model.

Although the embodiment above describes the parameterization function as a fourth order polynomial that satisfies the four boundary conditions, in other embodiments, the parameterization function is other types of functions that satisfy the four boundary conditions. In another embodiment, the parameterization function is a sinusoid function having a power of two or more. The sinusoid functions that have a power of two or more inherently satisfy the four boundary conditions. In one embodiment, the sinusoid function is represented by the following equation:

$$x = a \sin^2 \rho \qquad (10)$$

where a is the only unknown model parameter and $\rho$ is a displacement of the target location. Since the sinusoid function expressed in Eq. (10) only includes one unknown model parameter, only one model point (e.g., image) needs to be obtained to be applied to the sinusoid function to determine the unknown model parameter, a. Alternatively, more than one model points may be obtained.

In another embodiment, the sinusoid function is represented by the following equation:

$$x = a |\sin^3 \rho x| \qquad (11)$$

where a is the only unknown model parameter and $\rho$ is a displacement of the target location. Since the sinusoid function expressed in Eq. (11) only includes one unknown model parameter, only one model point (e.g., image) needs to be obtained to be applied to the sinusoid function to determine the unknown model parameter, a. Alternatively, more than one model points may be obtained.

In another embodiment, the sinusoid function is represented by the following equation:

$$x = a \sin^4 \rho \qquad (12)$$

where a is the only unknown model parameter and $\rho$ is a displacement of the target location. Since the sinusoid function expressed in Eq. (12) only includes one unknown model parameter, only one model point (e.g., image) needs to be obtained to be applied to the sinusoid function to determine the unknown model parameter, a. Alternatively, more than one model points may be obtained.

In the embodiments above, a first sample point of the target location is determined using an acquired image. As described above, since the parameterization function includes only one model parameter, only one image needs to be used. Although only one image may be used to determine the one model parameter, in other embodiments, more than one image may be acquired to develop the correlation model. Once the first sample point is determined, the shape of the constrained curve is determined using the parameterization function and the first sample point. The first sample point defines the amount of curve of the constrained curve between the first and second intersections.

Figure 9:
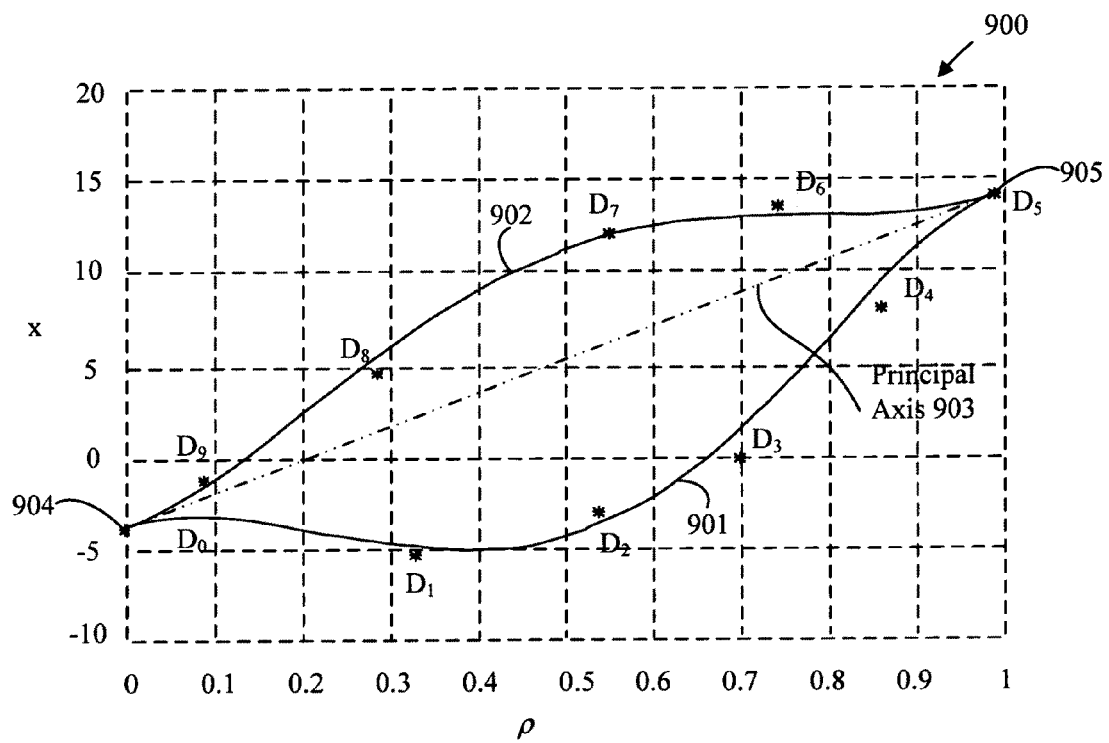
FIG. 9 is a graphical representation of an exemplary dual-constrained-curve correlation model of the path of movement in one dimension, as a function of movement of an external marker.

FIG. 9 is a graphical representation 900 of an exemplary dual-constrained-curve correlation model of the path of movement in one dimension, as a function of the displacement, p, of an external marker 25. In particular, the graph 900 shows the ($\rho$,x) coordinates from the data points $D_0$-$D_9$ and superimposes a dual-constrained-curve correlation model (solid line). Also, the displacement, $\rho$, is normalized to be between 0 and 1. The dual-constrained-curve correlation model also may be referred to herein as a constrained-curve correlation model and may include two or more constrained curves to approximate the target location. In another embodiment, the constrained-curve correlation model includes only one constrained curve. The approximate ($\rho$,x) coordinates corresponding to each of the data points $D_0$-$D_9$ is provided in Table 5 below.

TABLE 5

Data Point Coordinates.

| Data Point | ($\rho$, x) (mm) |
|---|---|
| $D_0$ | (0, −4) |
| $D_1$ | (0.33, −5) |
| $D_2$ | (0.54, −3) |
| $D_3$ | (0.7, 0) |
| $D_4$ | (0.86, 8) |
| $D_5$ | (0.99, 14) |
| $D_6$ | (0.73, 13.5) |
| $D_7$ | (0.55, 12.3) |
| $D_8$ | (0.28, 5) |
| $D_9$ | (0.09, −1) |

The constrained-curved correlation model may be used to estimate the x displacement of the target 10 based on the displacement, $\rho$, measured by the external marker 25.

The constrained-curved correlation model may be used to estimate the x displacement of the target 10 based on the displacement, $\rho$, measured by the external marker 25. The dual-constrained-curve correlation model has two constrained curves 901 and 902. Each of the constrained curves is defined by the parameterization function. In this embodiment, the parameterization function is the fourth order polynomial as set forth in the equation (9) above. As described above, the model parameter, a, is the only unknown model parameters and $\rho$ is the displacement of the target location. Since the simplified fourth order polynomial only includes one unknown model parameter, only one model point (e.g., image) needs to be obtained to be applied to the simplified equation to determine the unknown model parameter, a. Also, described above, the parameterization function satisfies the four boundary conditions. The first boundary condition is that the constrained curve (901 or 902) intersects the principal axis 903 at a first intersection 904. The second boundary condition is that the constrained curve (901 or 902) intersects the principal axis 903 at the second intersection 905. The third boundary condition is that the constrained curve (901 or 902) is tangent to the principal axis 903 at the first intersection 904. The fourth boundary condition is that the constrained curve (901 or 902) is tangent to the principal axis 903 at the second intersection 903. The principal axis 903 may be determined using a linear approximation of the data points of the external marker 25. The linear approximation may be done using a linear square fit or other known linear fits.

In another embodiment, the speed of the external marker's 25 motion (e.g., respiration motion) may be used to build a constrained-curve correlation model, as illustrated, that more closely approximates the organ path. The speed of the external marker may be determined by determining the derivative of the displacement, $\rho$ (e.g., respiration displacement. For example, using the speed of the external marker 25 may be useful in cases in which the target 10 takes different paths during the inspiration and expiration intervals, respectively, of the respiration period. In other embodiments, the displacement and/or speed of other motions, other than respiration, may be used in addition to or instead of the respiration. One example of an equation that takes into account both displacement, $\rho$, and speed, $\dot{\rho}$, as a second independent variable, is as follows:

$$x = f(\rho, \dot{\rho}) \qquad (13)$$

The constrained-curve correlation model may be used to estimate the x displacement of the target 10 based on the speed, $\dot{\rho}$, and the direction of motion (i.e., the positive or negative sign of $\dot{\rho}$) of the external marker 25. In one embodiment, the directional indicators may be used to split the path of movement of the target 10 into two separate paths, constrained curves 901 and 902. The directional indicators also may be used to distinguish the data points $D_1$-$D_4$ corresponding to the inspiration interval from the data points $D_6$-$D_9$ corresponding to the expiration interval.

In one embodiment, the foregoing equation essentially separates the data points into two separate groups according to their respective direction of motion of each data point. In particular, data points whose direction is positive (according to a predetermined sign convention) may be placed in a first data set and data points whose direction is negative may be placed in a second data set. The data sets may correspond to the inspiration and expiration intervals. However, in another embodiment, the data sets for each of the approximations may overlap. For example, data points that have a relatively small directional value may be placed in more than one data set, regardless of sign. As an example, the data points $D_0$, $D_4$, $D_5$, and $D_9$ may be placed in each of two data sets. Accordingly, the foregoing equations may be modified to account for these overlapping data sets. The outputs of parameterization function may be averaged for the data points that belong to more than one data set. In another embodiment, more than two parameterization functions may be used to approximate the movement of the target 10.

Although the embodiment above describes the parameterization function as a fourth order polynomial that satisfies the four boundary conditions, in other embodiments, the parameterization function is other types of functions that satisfy the four boundary conditions, such as sinusoid functions having a power of two or more.

In one embodiment, a linear fit approximation is used to determine the principal axis 903. Once the principal axis 903 is determined, the equation can be simplified by a simplification process, such as a detrending process, so that the computations of the model can be simplified. As a result, the principal axis 903 is set to be a horizontal line and scaled to have a specific value, such as 0. For example, the linear fit approximation can be subtracted from the equation so that the principal axis is on the horizontal line of x in the one dimension (x dimension), as illustrated in FIG. 10.

Figure 10:
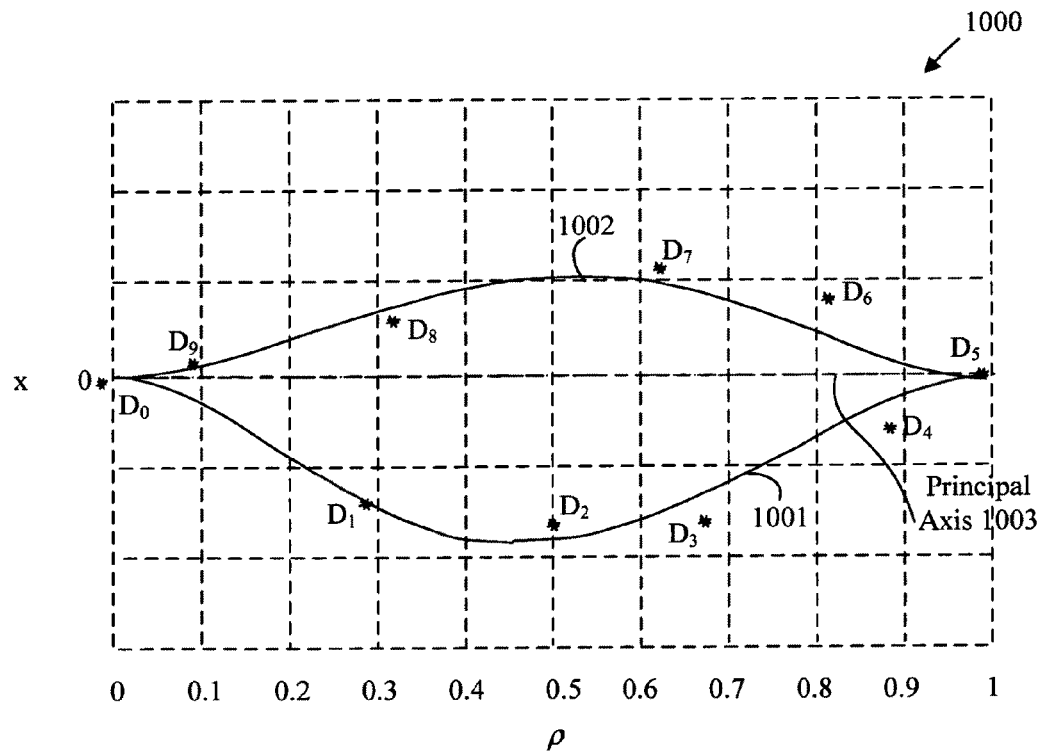
FIG. 10 is another graphical representation of the exemplary dual-constrained-curve correlation model of FIG. 9.

FIG. 10 is another graphical representation of the exemplary dual-constrained-curve correlation model of FIG. 9. In particular, the graph 1000 shows the ($\rho$,x) coordinates from the data points $D_0$-$D_9$ and superimposes a dual-constrained-curve correlation model (solid line) that has been simplified, for example, by removing the linear component from the original data, such as by using a detrending process. As part of the detrending process, the principal axis 903 is set to be a horizontal line and scaled to have a specific value, such as 0, as illustrated by the principal axis 1003. Also, the displacement, $\rho$, is normalized to be between 0 and 1. As a result, the principal axis 1003 is set to be horizontal at x=0, and each of the constrained curves are set to intersect the principal axis 1003 at the horizontal principal axis 1003 at $\rho$=0 and $\rho$=1. For the first two boundary conditions, each of the constrained curves 901 and 902 intersects the principal axis at two intersections. For the other two boundary conditions, each of the constrained curves 901 and 902 is tangent to the principal axis 1003 at the two intersections. In particular, the speed of the displacement, $\dot{\rho}$, (e.g., derivative) at $\rho$=0 and $\rho$=1 are both zero $\left(\text{e.g., } \frac{dx}{d\rho} = 0\right)$.

These four boundary conditions of each constrained curve reduces the number of model points (e.g., images) needed to develop the correlation model, which results in a decrease in unnecessary imaging occurrences. By using the constrained curve that satisfies these four boundary conditions, the correlation model does not have problems when approximating the target locations at the boundary regions corresponding to the moments between the inspiration and expiration periods. By using a constrained curve that satisfies these four boundary conditions, the shape of the curves at the boundary regions is already determined as part of the correlation model. Also, by using a constrained curve that satisfies these four boundary conditions, no matching approximations or blending is required to link the inspiration and expiration approximations. In addition, the shape of the constrained curve can be determined using the parameterization function (that satisfies the four boundary conditions) and a single sample point (e.g., image). The single sample point defines the amount of curve of the constrained curve between the two intersections.

Figure 11:
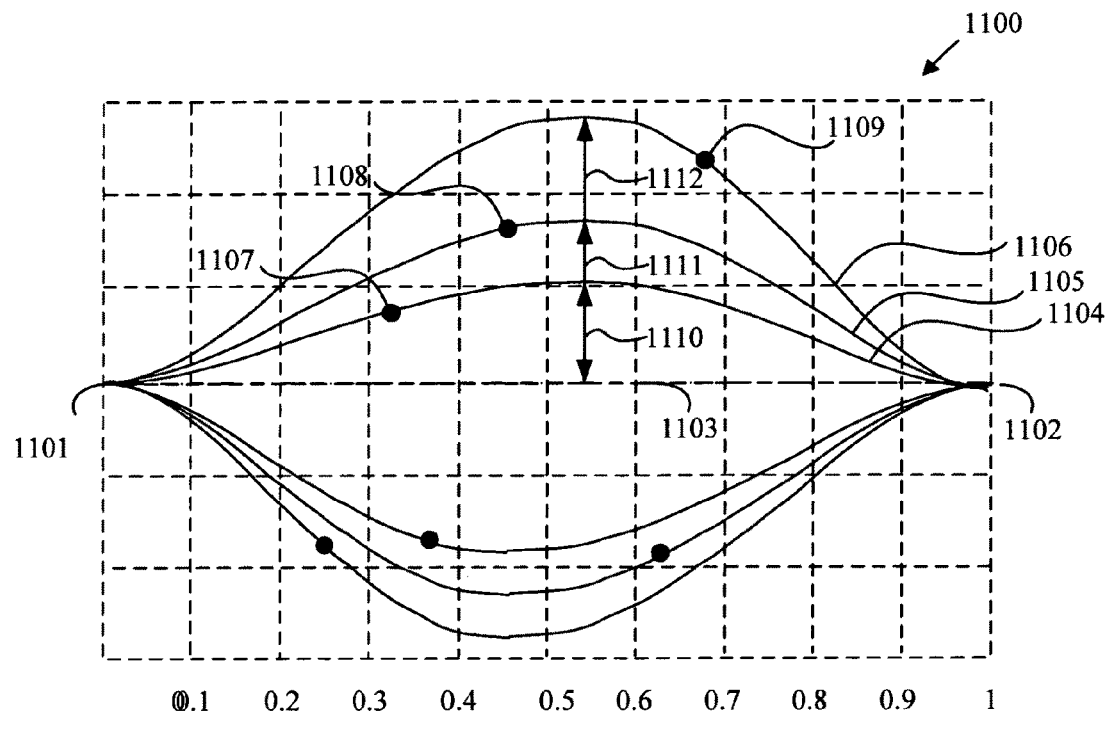
FIG. 11 is a graphical representation of an exemplary respiration signal over time representative of changes in respiration behavior.

FIG. 11 is a graphical representation of exemplary constrained curves having sample points that each defines an amount of curve for the exemplary constrained curves. Since the shape of the constrained curve is already defined by the parameterization function that satisfies the four boundary conditions, one model point (e.g., image) may be used to define the amount of curve (also referred to as the amount of bulge) of the constrained curve between the first and second intersections. For example, graph 1100 includes various constrained curves that each intersects the principal axis 1103 at the two intersections 1101 and 1102, and each of the constrained curves is tangent at both intersections 1101 and 1102. For example, if the one sample point 1107 is obtained, then the constrained curve has a first amount of curve, as illustrated by the constrained curve 1104. Similarly, if the one sample point 1108 is obtained, then the constrained curve has a second amount of curve that is greater than the first amount of curve, as illustrated by the constrained curve 1105. And, if the one sample point 1109 is obtained, then the constrained curve has a third amount of curve that is greater than the first and second amounts of curve. Likewise, single sample points can be obtained to define the amount of curve of the corresponding constrained curve for the return path (illustrated in FIG. 11 as the constrained curves that are below the principal axis 1103). Since the parameterization function that satisfies the four boundary conditions already determines the shape of the constrained curve, the model point (e.g., image) can be used to define the amount of curve (e.g., bulge) of the constrained curve. It should be noted that although FIG. 11 illustrates three constrained curves above the principal axis 1103 and three constrained curves below the principal axis 1103, only one constrained curve may be used, or alternatively, two constrained curves may be used, one from above and one from below the principal axis 1103. In one embodiment, the constrained curve is symmetrical about a vertical axis. In another embodiment, the constrained curve is asymmetrical about the vertical axis. Also, as previously discussed the constrained curve above the principal axis 1103 may not be symmetrical about the principal axis 1103, since the target 10 may move in different paths, for example, paths of the target 10 during the inspiration and expiration periods.

In one embodiment, the amount of curve of a constrained curve can be measured by the maximum height of the constrained curve. For example, the constrained curves 1104, 1105, and 1106, as defined by the model points 1107, 1108, and 1109, respectively, have heights 1110, 1111, and 1112, respectively. Alternatively, the amount of curve of the constrained curve can be measured using other methods.

In another embodiment, using the constrained curve that satisfies the four boundary conditions, the correlation model can be adapted in response to changes of behavior in the movement of the target 10, such as respiration behavior. In one embodiment, when the data points of the external marker 25 exceed the values of the model points of the correlation model, the correlation model includes a linear approximation (e.g., linear fit) that provides values that are outside the constrained curves (e.g., values that are not between the two intersections). This may be done instead of expanding the constrained curves beyond the sample model points (e.g., images). However, when there is a significant changes in behavior, the correlation model can scale down (e.g., shrink) the constrained curve(s) to accommodate changes in behavior. Although the correlation model can be expanded (e.g., scaled up), typically, the correlation model should only shrink (e.g., scaled down), not expand.

Figure 12:
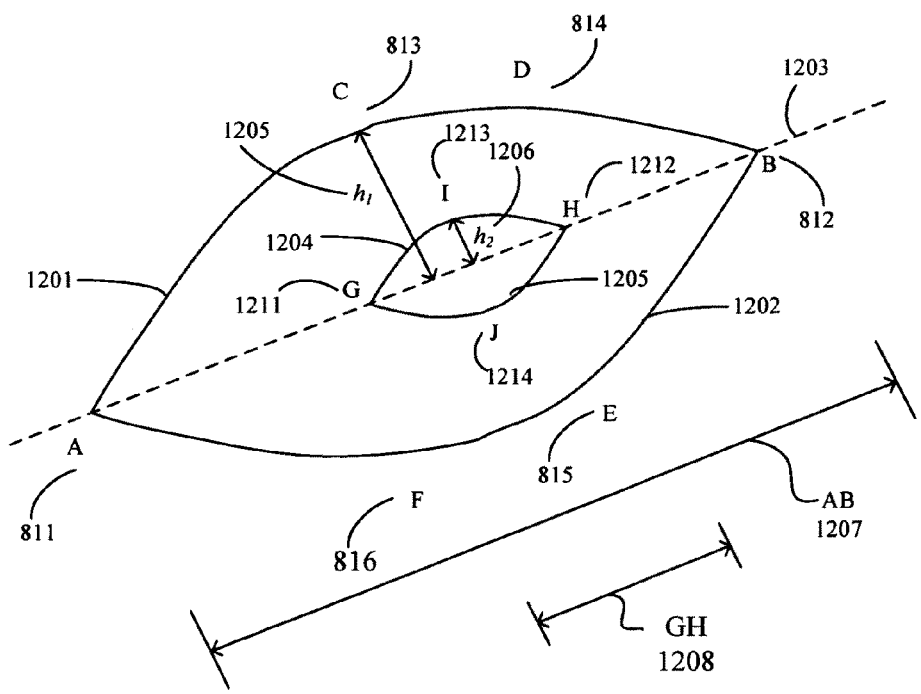
FIG. 12 is a graphical representation of an exemplary estimated path for a dual-constrained-curve correlation model when there is the change in respiration behavior of FIG. 11.

FIG. 12 is a graphical representation of an exemplary estimated path for a dual-constrained-curve correlation model when there is the change in respiration behavior of FIG. 8B. Like the correlation model of FIG. 8C, the correlation model of FIG. 12 provides output that is continuous along the constrained curve 1201 from point A 811 to point B 812 and from point B 812 back to the point A 811 on the other constrained curve 1202 in a continuous manner. However, as the respiration signal 802 of FIG. 8B changes from the first respiratory behavior, unlike the correlation model of FIG. 8C that jumps from the one curve to the other in a discontinuous manner, such as from point D 814 to point E 815 and between point F 816 and point C 813, the correlation model of FIG. 12 shrinks to provide continuous output along the scaled-down constrained curve 1204 from point G 1211 to point H 1212 through point I 1213 and from the point H 1212 to the point G 1211 through point J 1214 on the other constrained curve 1205.

As described above, the changes in the respiration behavior 803 may have different characteristics than the first respiration behavior, such as different magnitudes, different frequency, or the like. For example, the respiration signal 802 during times $t_1$ 805 and $t_5$ 809 has a smaller magnitude of displacement than the respiration signal 802 before the time $t_1$ 805. As a result, using the scaled-down constrained curves, the model output will be correct when there is a change in respiration behavior. For example, at time $t_4$ 808 the model output will be a smaller value as expected, since the magnitude of the displacement at the time $t_4$ 808 is smaller in magnitude than the un-scaled correlation model, which is based on the magnitude of displacement of the first respiration behavior. Also, using the scaled-down constrained curves, the model output is continuous despite the change in respiration behavior 803. For example, instead of the model output jumping from the inspiration approximation curve to the expiration approximation curve in a discontinuous manner, as illustrated in FIG. 8C, the correlation model of FIG. 12 provides continuous output from the scaled-down constrained curves. Similarly, when the respiration behavior change to be more like the first respiration behavior, the correlation model can be expanded (e.g., scaled up) to be more like the original correlation model. Also, using the scaled-down constrained curves, there is no discontinuity in the model output that causes non-optimal motion of the LINAC 20. As described above, the motion of the LINAC 20 can be synchronized to the movements of the target 10, and as such, discontinuity in the model output can disturb the expected continuous motion of the LINAC 20. For example, the LINAC 20 may jerk, accelerate, decelerate, jolt, or the like, in response to synchronizing its motion to the discontinuous model output.

In one embodiment, at the respiratory boundary, at the first intersection of ρ=0, the value of x is zero and the derivative at the intersection is zero $$\left( e.g., x = 0 \text{ and } \frac{dx}{d\rho} = 0 \right),$$

and at the second intersection of ρ=1, the value of x is zero and the derivative at the intersection is zero $$\left( e.g., x = 0 \text{ and } \frac{dx}{d\rho} = 0 \right).$$

The values of ρ are normalized to be within the region between ρ=0 and ρ=1, and the linear component has been removed from the original data, such as illustrated in FIG. 10. Due to the simplicity of the correlation model (e.g., has only one unknown model parameter for each constrained curve by satisfying the four boundary conditions), it is easier than conventional methods and systems to adapt the correlation model for significant changes in movement behavior.

In one embodiment, the correlation model is adapted by using a shrinking algorithm. The shrinking algorithm is configured to automatically adapt the original correlation model to the changes in the movements, as described above with respect to FIG. 12. The real values of the correlation model should be on track of the smaller constrained curves 1204 and 1205 (e.g., points G-I-H-J), instead of jumping between the curves without shrinking (e.g., points C-D-E-F), as described with respect to FIG. 8C. In one embodiment, using the shrinking algorithm, at time $t_1$ 805 the correlation model is updated and the only model parameter, a, is recorded. The height, $h_1$, is the height of the correlation model. The height, $h_1$, for example, may be the distance from the constrained curve 1201 at point C 813 to the principal axis 1203. Alternatively, the height, $h_1$, may be measured from other points. In one embodiment, the relationship between the model parameter, a, and $h_1$, is set forth in the following equation:

$$a = 16 * h_1 \tag{14}$$

Before time $t_1$ 805, the current range of movement (e.g., respiration range) may be measured as the distance AB 1207 between point A 811 and point B 812. This range may be the range between the maximum and minimum displacement values. When the current range of movement is smaller than the range of the original correlation model at the update (e.g., distance AB 1207), the current range of movement can be used to determine a new value for the model parameter, a. For example, when the current range of movement is measured as the distance GH 1208 between point G 1211 and point H 1212, the current range of movement is used to determine a new value for the model parameter, a. The constrained curves 1201 and 1202 are assumed to be proportional to the constrained curves 1204 and 1205. This proportional relationship is set forth in the following equation:

$$h_2 = h_1 * \frac{GH}{AB} \tag{15}$$

When using the shrinking algorithm, within the regions between points A 811 and G 1211 and the points H 1212 and B 812, a linear model can be used, providing output that is on the principal axis 1203 between the points A 811 and G 1211 and the points H 1212 and B 812. However, within the region between points G 1211 and H 1212, the scaled-down constrained curves 1204 and 1205, with the new height, $h_2$, are used. The new height, $h_2$, is measured, for example, from point I 1213 to the principal axis 1203, and may be determined using the proportional relationship between AB 1207 and GH 1208. As such, with the dual-constrained-curve correlation model having the shrinking algorithm, not only are the correct model values obtained, the model provides continuous output, even in situations of non-trivial varying respiratory behavior. The current range is measured for each respiration cycle. A change to the correlation model, i.e. the shrinking algorithm, is made if the change in respiration is significant. In one embodiment, the change in respiration is considered to be significant if it is more than 10%. In another embodiment, other percentages can be used to decide whether the change in respiration is significant.

It should be noted that although the embodiments above are described as changes in respiration behavior, in other embodiments, the changes in behaviors in other types of movements can be compensated. For example, instead of tracking the respiration signal 802 of a respiratory cycle, other waveforms of other periodic motions of the patient can be tracked, such as, for example, movement of the target 10 caused by a heart beat.

Figure 13:
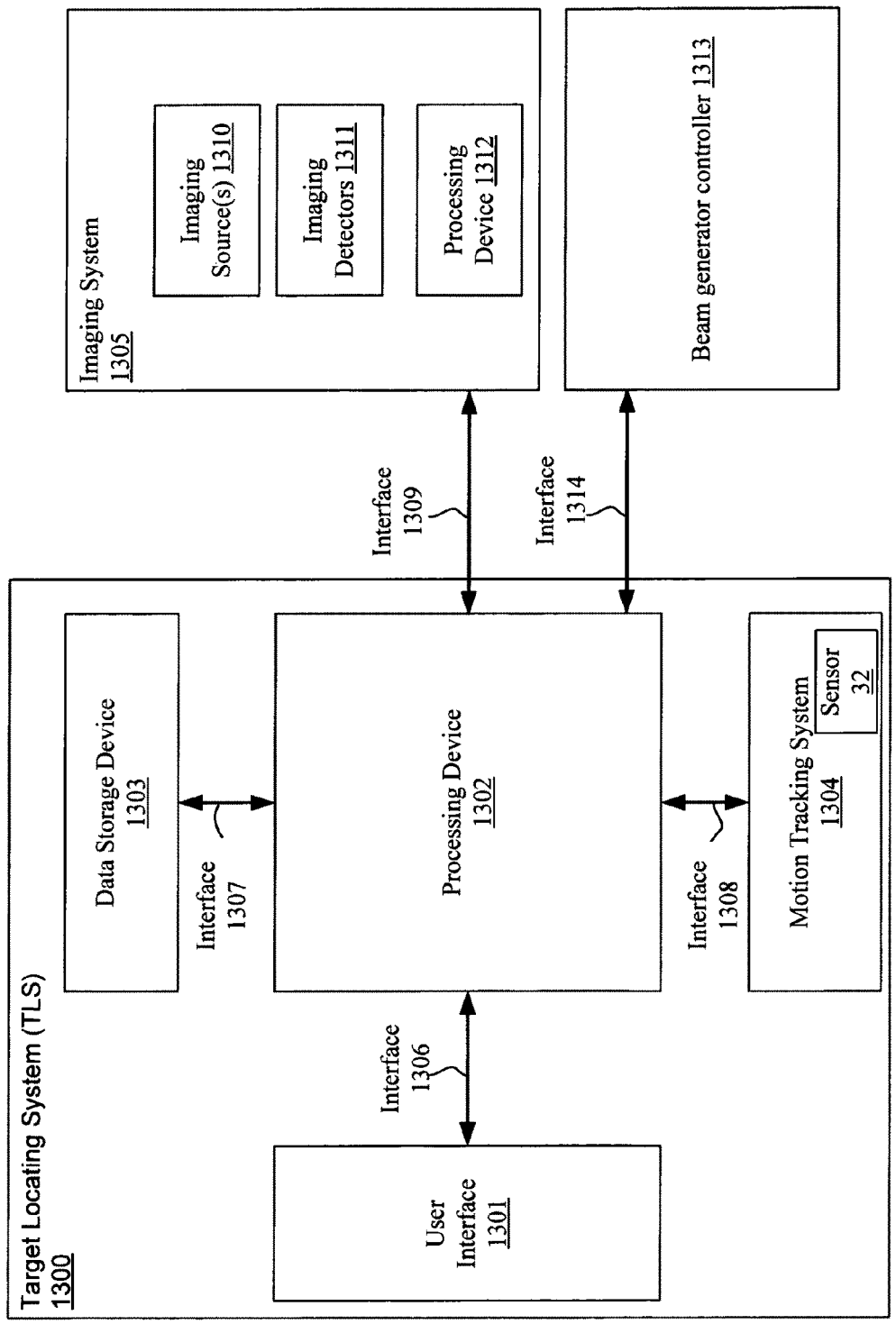
FIG. 13 illustrates a block diagram of one embodiment of a target locating system for developing a dual-constrained-curve correlation model.

FIG. 13 illustrates a block diagram of one embodiment of a target locating system 1300 for developing a dual-constrained-curve correlation model. The target locating system 1300 includes a user interface 1301, a processing device 1302, a data storage device 1303, and a motion tracking system 1304. The user interface 1306, the data storage device 1303, and the motion tracking system 1304 are each coupled to the processing device 1302 by interfaces 1306, 1307, and 1308, respectively. The target locating system 1300 is coupled to an imaging system 1305 via interface 1309. The imaging system 1305 includes one or more imaging sources 1310, one or more corresponding imaging detectors 1311, and an image controller 1312. The imaging sources 1310, imaging detectors 1311, and the image controller 1312 are coupled to one another via a communication channel (not illustrated), such as a bus.

Figure 16:
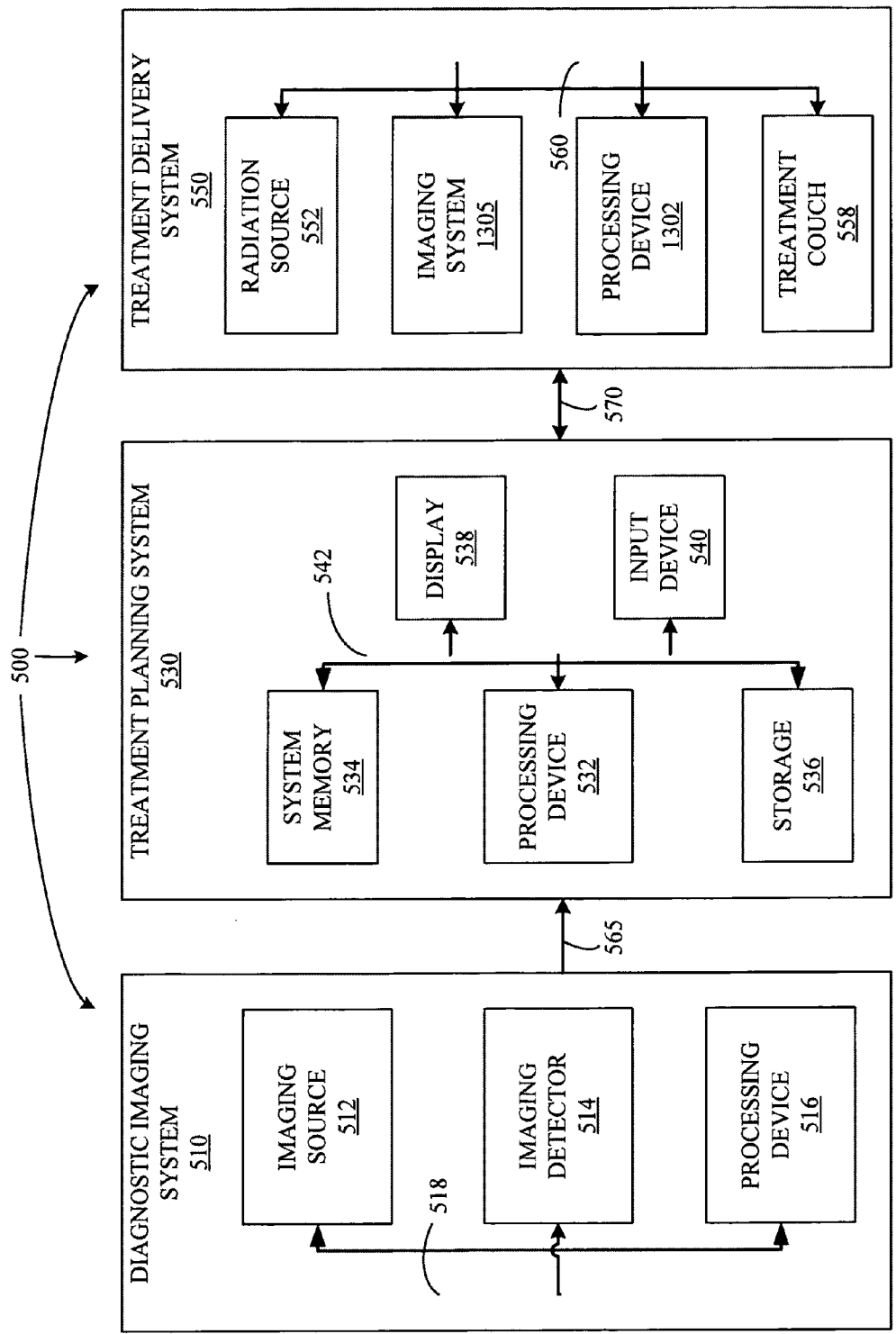
FIG. 16 illustrates one embodiment of a treatment system that may be used to perform radiation treatment in which embodiments of the present invention may be implemented.

The user interface 1301 may include a display, such as display 538 described in FIG. 16, one or more input devices, such as keyboard, mouse, trackball, or similar device, to communicate information, to select commands for the processing device 1302, to control cursor movements on the display, or the like. The user interface 1301 is configured to allow user interaction in developing the correlation model, such as when to acquire a model point (e.g., image) to develop the initial correlation model, or when to update the correlation model. In one embodiment, the user interface 1301 is a graphical user interface (GUI) that includes an "Acquire" button. Upon selecting the "Acquire" button, the user interface 1301 sends an acquire command to the processing device 1302. The processing device 1302, in response, automatically determines the phases of the respiratory cycle at which to acquire images, and automatically triggers the imaging system 1305 to acquire the images at the determined time. In another embodiment, the user interface 1301 provides a window with a generic graph of the respiratory cycle with multiple input devices (e.g., radio input buttons) to select a phase (e.g., location) of the respiratory cycle. In response, the processing device 1302 automatically acquires the model point (e.g., image) at the indicated phase of the respiratory cycle. This may be repeated for other phases of the respiratory cycle.

In another embodiment, the user interface 1301 provides visual feedback of the positional data of the one or more external markers 25, actual locations of the respiratory cycle where images have been acquired, or the like. In another embodiment, the user interface 1301 includes a button that automatically acquires the images at substantially evenly-distributed phases of the respiratory cycle, and automatically develops the correlation model based on the automatically acquired images. In another embodiment, the user interface 1301 is used to manually trigger the acquisition of one or more images for sample model points in developing the correlation model. Alternatively, the user interface 1301 may include more or less user-interface mechanisms than those described above to allow the user to interact with the target locating system 1300 to acquire one or more images.

In one embodiment, the imaging source 1310 generates an imaging beam (e.g., X-rays, ultrasonic waves, radio frequency waves, etc.) and the imaging detector 1311 detects and receives the imaging beam. Alternatively, the imaging detector 1311 may detect and receive a secondary imaging beam or an emission stimulated by the imaging beam from the imaging source (e.g., in an MRI or PET scan). In one embodiment, the diagnostic imaging system 510 may include two or more diagnostic imaging sources 1310 and two or more corresponding imaging detectors 1311. For example, two X-ray sources 1310 may be disposed around a patient to be imaged, fixed at an angular separation from each other (e.g., 90 degrees, 45 degrees, etc.) and aimed through the patient toward corresponding imaging detectors 1311, which may be diametrically opposed to the imaging sources 1311. A single large imaging detector 1311, or multiple imaging detectors 1311, also may be illuminated by each X-ray imaging source 1311. Alternatively, other numbers and configurations of imaging sources 1310 and imaging detectors 1311 may be used.

The imaging source 1310 and the imaging detector 1311 are coupled to the image controller 1312, which controls the imaging operations and process image data within the imaging system 1305. In one embodiment, the processing device 516 communicates with the imaging source 512 and the imaging detector 514. Embodiments of the processing device 516 may include one or more general-purpose processors (e.g., a microprocessor), special purpose processors such as a digital signal processor (DSP), or other type of devices such as a controller or field programmable gate array (FPGA). The processing device 516 also may include other components (not shown) such as memory, storage devices, network adapters, and the like. In one embodiment, the processing device 516 generates images (e.g., diagnostic and/or intra-treatment images) in a standard format such as the Digital Imaging and Communications in Medicine (DICOM) format. In other embodiments, the processing device 516 may generate other standard or non-standard digital image formats.

The motion tracking system 1304 is configured to track and compensate for the motion of the target 10 with respect to the radiation source of the LINAC 20 (not illustrated in FIG. 13). The motion tracking system 1304 includes one or more tracking sensors 32 that track the location of one or more external markers 25. For example, the tracking sensor 32 may track upward movement of the external marker 25 during the inspiration interval and downward movement of the external marker 25 during the expiration interval. The relative position of the external marker 25 is correlated with the location of the target 10, so that the LINAC 20 may move relative to the location of the external marker 25 and the correlated location of the target 10. In another embodiment, other types of external or internal markers may be used instead of, or in addition to, the illustrated external marker 25.

As one example, the depicted target 10 is shown four positions designated as $D_0$, $D_3$, $D_5$, and $D_7$, as illustrated and described with respect to FIG. 1. As the patient breathes, the target 10 may move along a path within the patient's body. In one embodiment, the path of the target 10 is asymmetric in that the target 10 travels along different paths during the inspiration and expiration intervals. In another embodiment, the path of the target 10 is at least partially non-linear. The path of the target 10 may be influenced by the size and shape of the target 10, organs and tissues surrounding the target 10, the depth or shallowness of the patient's breathing, and so forth. By correlating the positions of the external marker 25 to the target 10, the position of the target 10 may be derived from the position of the external marker 25 even though the external marker 25 may travel in a direction or along a path that is substantially different from the path and direction of the target 10. The LINAC 20 is also shown in a first position, $D_0$, a second position, $D_3$, a third position, $D_5$, and a fourth position, $D_7$, which also correspond to the positions of the target 10, as described and illustrated with respect to FIG. 1. In this way, the movements of the LINAC 20 may be substantially synchronized to the movements of the target 10 as the position of the target 10 is correlated to the sensed position of the external marker 25.

Tracking the position of the target 10 using motion tracking system 1304 may be performed in a number of ways. Some exemplary tracking technologies include fiducial tracking, soft-tissue tracking, and skeletal structure tracking, which are known in the art; accordingly, a detailed discussion is not provided.

In one embodiment, the motion tracking system 1304 is the SYNCHRONY® respiratory tracking system, developed by Accuray, Inc., Sunnyvale, Calif. Alternatively, other motion tracking systems may be used.

In one embodiment, the motion tracking system 1304 is used in conjunction with the processing device 1302 of the treatment delivery system 1300 to deliver radiation beams to a target whose surrounding tissue is moving with respiration during treatment delivery. The motion tracking system 1304 tracks motion of one or more external markers 25 (not illustrated in FIG. 13) that are disposed on the patient. The motion tracking system 1304 also is configured to compensate for the motion of the target immediately before or during treatment delivery. In compensating for the motion of the target, motion tracking system 1304 determines the movement of the one or more external markers 25 over time. The movement of the one or more external markers 25 may be sent to the processing device 1302 for processing and to the storage device 1303 to be stored in a data set for developing or updating the correlation model. In one embodiment, the LINAC 20, which includes the radiation source 106, is moved to compensate for the motion of the target 10, as determined by the TLS 1300. For example LINAC 20 may move to keep the source-to-axis (SAD) fixed, based on the calculations made by the motion tracking system 1304 or the processing device 1302. Alternatively, the LINAC 20 is stationary, and the motion tracking system 1304 determines a different value for the SAD.

In one embodiment, the data storage device 1303 stores multiple displacement points of the monitored, external marker 25. The displacement points are indicative of the motion of the external marker 25 during a respiratory cycle of a patient. The processing device 1302 is configured to identify linear or non-linear paths of movement of the target using a parameterization function to approximate the non-linear path of movement. The parameterization function, as described above, includes a constrained curve that intersects a principal axis at first and second intersections. Also, the constrained curve is tangent to the principal axis at the first and second intersections. The processing device 1302 is also configured to develop a correlation model of the non-linear path of movement using the parameterization function and at least one image as the sample model point. As described herein, the parameterization function also satisfies the four boundary conditions. In one embodiment, the processing device 1302 receives a first acquired image from the data storage device 1303, or directly from the imaging system 1305, and determines a first sample point. Using the parameterization function and the first sample point, the processing device 1302 determines a shape of the constrained curve. As described above, the first sample point defines an amount of curve of the constrained curve between the first and second intersections.

In one embodiment, the parameterization function is a fourth order polynomial that has only one unknown model parameter, as described above. In another embodiment, the parameterization function is a sinusoid function having a power of two or more that inherently satisfies the four boundary conditions. The sinusoid function also has only one unknown model parameter, as described above.

In another embodiment, the processing device 1302 is configured to detect a change in magnitude of the movement of the external marker 25 and to scale the correlation model when the change in magnitude is detected, as described above with respect to FIG. 12.

In another embodiment, the processing device 1302 is configured to identify an inspiration interval of the non-linear path of movement of the target that is associated with an approximate time during which the patient breathes in, and an expiration interval of the non-linear path of movement of the target that is associated with an approximate time during which the patient breathes out. The non-linear path of movement of the target includes both an inspiration path associated with the inspiration interval and an expiration path associated with the expiration interval. The positions of the external marker 25 define an external path of movement of the external marker 25. The external path of movement has a respiratory period associated with a respiratory cycle of the patient.

In another embodiment, the processing device 1302 is configured to determine a derivative of the data points of the positions of the external marker 25 of the non-linear path. The derivative of the data points may be the speed of movement of the external marker 25 and may identify whether the data point is part of the inspiration interval or the expiration interval of the respiratory period. The derivative may include a directional indicator.

In another embodiment, the processing device 1302 is configured to develop a correlation model that includes a dual-constrained curve. For example, a first constrained curve associated with the non-linear path of movement of the target over the inspiration interval and a second constrained curve associated with the non-linear path of movement of the target over the expiration interval. Alternatively, the constrained curves are representative of movements of the target 10 caused by other periodic motions of the patient, such as heartbeats. The processing device 1302 uses the correlation model to derive a target position of the target.

In addition to storing the displacement points, the storage device 1303 may be configured to store the image data of the images acquired by the imaging system 1305. The processing device 1302 uses the images and the displacement points to generate the correlation model.

In another embodiment, the imaging system 1305, under control of the processing device 1302 or image controller 1312, periodically generates positional data about the target by automatically acquiring images of the target during treatment, and the motion tracking system 1304 continuously generates positional data about the external motion of the one or more external markers 25 during treatment. The positional data about the target and the positional data about the external motion of the external marker 25 are used to update the correlation model. The timing of the image acquisition of the images during treatment may also be automatically controlled by the processing device 1302 so that the images are acquired at specified times (corresponding to specified phases) of the respiratory cycle. In one embodiment, the correlation model is generated immediately before treatment using one or more pretreatment images acquired by the imaging system 1305 and displacement points acquired by the motion tracking system 1304. During treatment, a current position of the target is determined using the correlation model. Additional images and displacement points may be acquired, and the correlation model is updated based on the additional images and displacement points.

In one embodiment, in order to acquire images, the processing device 1302 sends a trigger command or signal to the imaging system 1305 on interface 1309.

The processing device 210 is also configured to derive a target position of the target based on the correlation model, and to send a position signal associated with the target position to a beam generator controller 1313, which controls the radiation source of the LINAC 20 to direct a beam at the target, via an interface 1314. In this way, the movements of the LINAC 20 may be substantially synchronized to the movements of the target 10 as the position of the target 10 is correlated to the sensed position of the external marker 25.

In another embodiment, the processing device 1302 is part of the motion tracking system 1304 and interfaces with the imaging system 1305 to identify the non-linear path and/or develop the correlation model using the parameterization function, as described above. Alternatively, other configurations of the processing device 1302, motion tracking system 1304, and the imaging system 1305 may be used.

Figure 14:
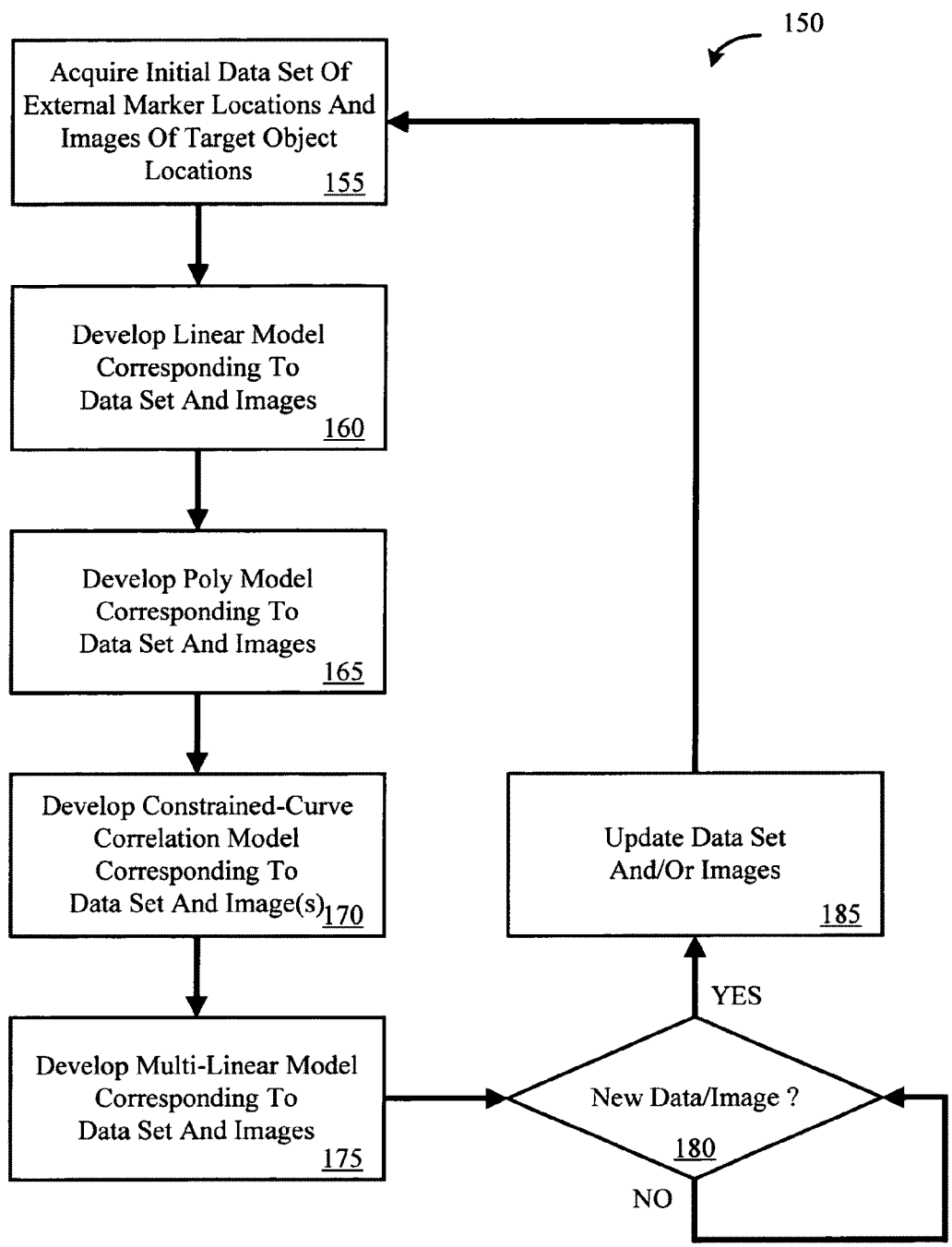
FIG. 14 illustrates one embodiment of a modeling method.

FIG. 14 illustrates one embodiment of a modeling method 150. In one embodiment, the modeling method 150 may be implemented in conjunction with a treatment system such as the treatment system 500 of FIG. 16. Furthermore, the depicted modeling method 150 may be implemented in hardware, software, and/or firmware on a treatment system 500, such as the treatment planning system 530 or the treatment delivery system 550. Although the modeling method 150 is described in terms of the treatment system 500, embodiments of the modeling method 150 may be implemented on another system or independent of the treatment system 500. In one embodiment, the depicted modeling method 150 is implemented in hardware, software, and/or firmware on a treatment planning system, such as the treatment planning system 530 of FIG. 16. Although the modeling method 150 is described in terms of the treatment planning system 530, embodiments the modeling method 150 may be implemented on another system or independent of the treatment planning system 530.

The illustrated modeling method 150 begins and the treatment planning system 530 acquires an initial data set of locations of an external marker 25, operation 155. As part of operation 155, the treatment planning system 530 also automatically or manually acquires 155 one or more images of the target 10. The location of the target 10 may be derived from these images. The position of the target 10 may also be determined relative to the location of the external marker 25.

The treatment planning system 530 subsequently uses the data set and images to develop a linear correlation model as described above, operation 160. The treatment planning system 530 also uses the data set and images to develop a non-linear polynomial correlation model as described above, operation 165. The treatment planning system 530 also uses the data set and images to develop a constrained-curve correlation model as described above, operation 170. The treatment planning system 530 also uses the data set and images to develop a multi-linear correlation model, operation 175. The multi-linear correlation model includes a linear model for the inspiration and a linear model for the expiration. Although the illustrated modeling method 150 develops several types of correlation models, other embodiments of the modeling method 150 may develop fewer or more correlation models, including some or all of the correlation models described herein. Also, it should be noted that only one image may be used to develop the constrained-curve correlation model of operation 170. The different types of correlation models are known to those of ordinary skill in the art, and additional details regarding these types of correlation models have not been included so as to not obscure the embodiments of the present invention.

The treatment planning system 530 maintains these correlation models and, in certain embodiments, monitors for or acquires new data and/or images. When new data or images are received, operation 180, the treatment planning system updates the data set and or the images, operation 185, and may iteratively develop new models based on the new information. In this way, the modeling method 150 may maintain the correlation models in real-time.

It should be noted that the method 150 may also be performed in the treatment delivery system 550 described with respect to FIG. 16, or the target locating system described with respect to FIG. 13.

As part of the method in another embodiment, the treatment planning system 530 determines if the displacement of the external marker 25 is within the boundaries of the various correlation models. For example, many of the correlation models described above have a displacement range between approximately zero and 30 mm. A patient may potentially inhale or exhale in a way that moves the external marker 25 outside of a correlation model range. If the displacement of the external marker 25 is not within the range of the correlation models, then the treatment planning system 530 may select the linear correlation model and extrapolate outside of the model boundaries. Alternatively, the treatment planning system 530 may select another correlation model such as the multi-linear correlation model and determine an estimated location of the target 10 from the selected correlation model. In another embodiment, if the displacement of the external marker 25 is not within the range of the constrained-curve correlation model, then the treatment planning system 530 may use the shrinking algorithm, as described herein to adapt (e.g., scale) the constrained-curve correlation model.

Figure 15:
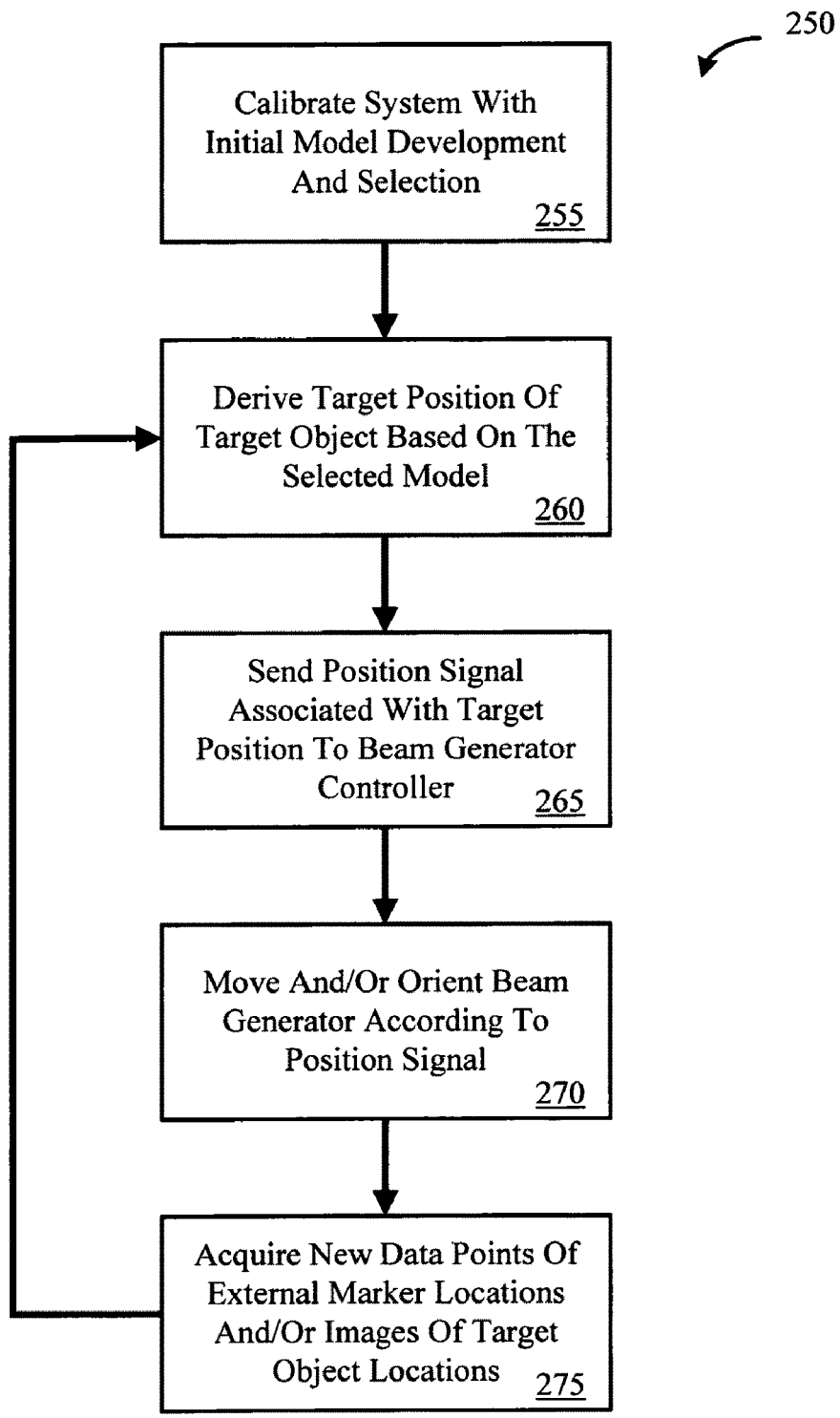
FIG. 15 illustrates one embodiment of a tracking method.

FIG. 15 illustrates one embodiment of a tracking method 250. In one embodiment, the tracking method 250 is implemented in conjunction with a treatment system such as the treatment system 500 of FIG. 16. Furthermore, the depicted tracking method 250 may be implemented in hardware, software, and/or firmware on a treatment system 500. Although the tracking method 250 is described in terms of the treatment system 500, embodiments of the tracking method 250 may be implemented on another system or independent of the treatment system 500.

The illustrated tracking method 250 begins and the treatment system 500 performs calibration to initialize model development and selection, operation 255. In one embodiment, such calibration includes performing the modeling method 150 prior to treatment delivery. In another embodiment, the modeling method 150 is performed multiple times to establish historical data.

After the tracking system 500 is calibrated, the tracking system 500 derives a target position of the target 10 based on the selected correlation model, operation 260. As described above, the target location of the target 10 may be related to the known position of the external marker 25 and derived from one of the correlation models. The tracking system subsequently sends a position signal indicating the target position to a beam generator controller (e.g., beam generator controller 1313 of FIG. 13), operation 265. In one embodiment, the treatment system 500 delivers the position signal to a treatment delivery system, such as the treatment delivery system 550 of FIG. 16. The treatment delivery system 550 then moves and orients the beam generator, such as the radiation source 552 of FIG. 16, operation 270. The treatment delivery system 550 and radiation source 552 are described in more detail below.

The treatment planning system 530 continues to acquire new data points of the external marker 25 and new images of the target 10 at a random phase or a specified phase of the respiratory cycle, operation 275. In one embodiment, the treatment planning system 530 may repeatedly develop models according to the modeling method 150 and select a model, as described above. In another embodiment, the treatment planning system 530 may select and use one model to derive multiple target positions. The tracking method 250 may continue in this manner of developing one or more models, selecting a model, and delivering treatment according to the selected model for the duration of a treatment session.

FIG. 16 illustrates one embodiment of a treatment system 500 that may be used to perform radiation treatment in which features of the present invention may be implemented. The depicted treatment system 500 includes a diagnostic imaging system 510, a treatment planning system 530, and a treatment delivery system 550. In other embodiments, the treatment system 500 may include fewer or more component systems.

The diagnostic imaging system 510 is representative of any system capable of producing medical diagnostic images of a volume of interest (VOI) in a patient, which images may be used for subsequent medical diagnosis, treatment planning, and/or treatment delivery. For example, the diagnostic imaging system 510 may be a computed tomography (CT) system, a magnetic resonance imaging (MRI) system, a positron emission tomography (PET) system, an ultrasound system, or another similar imaging system. For ease of discussion, any specific references herein to a particular imaging system such as a CT X-ray imaging system is representative of the diagnostic imaging system 510, generally, and does not preclude other imaging modalities, unless noted otherwise. In one embodiment, the diagnostic imaging system 510 is similar to the imaging system 1305, described with respect to FIGS. 9 and 14. In another embodiment, the diagnostic imaging system 510 and the imaging system 1305 are the same imaging system.

The illustrated diagnostic imaging system 510 includes an imaging source 512, an imaging detector 514, and a processing device 516. The imaging source 512, imaging detector 514, and processing device 516 are coupled to one another via a communication channel 518 such as a bus. In one embodiment, the imaging source 512 generates an imaging beam (e.g., X-rays, ultrasonic waves, radio frequency waves, etc.) and the imaging detector 514 detects and receives the imaging beam. Alternatively, the imaging detector 514 may detect and receive a secondary imaging beam or an emission stimulated by the imaging beam from the imaging source (e.g., in an MRI or PET scan). In one embodiment, the diagnostic imaging system 510 may include two or more diagnostic imaging sources 512 and two or more corresponding imaging detectors 514. For example, two X-ray sources 512 may be disposed around a patient to be imaged, fixed at an angular separation from each other (e.g., 90 degrees, 45 degrees, etc.) and aimed through the patient toward corresponding imaging detectors 514, which may be diametrically opposed to the imaging sources 514. A single large imaging detector 514, or multiple imaging detectors 514, also may be illuminated by each X-ray imaging source 514. Alternatively, other numbers and configurations of imaging sources 512 and imaging detectors 514 may be used.

The imaging source 512 and the imaging detector 514 are coupled to the processing device 516, which controls the imaging operations and process image data within the diagnostic imaging system 510. In one embodiment, the processing device 516 may communicate with the imaging source 512 and the imaging detector 514. Embodiments of the processing device 516 may include one or more general-purpose processors (e.g., a microprocessor), special purpose processors such as a digital signal processor (DSP), or other type of devices such as a controller or field programmable gate array (FPGA). The processing device 516 also may include other components (not shown) such as memory, storage devices, network adapters, and the like. In one embodiment, the processing device 516 generates digital diagnostic images (also referred to herein as pretreatment images) in a standard format such as the Digital Imaging and Communications in Medicine (DICOM) format. In other embodiments, the processing device 516 may generate other standard or non-standard digital image formats.

Additionally, the processing device 516 may transmit diagnostic image files such as DICOM files to the treatment planning system 530 over a data link 560. In one embodiment, the data link 560 may be a direct link, a local area network (LAN) link, a wide area network (WAN) link such as the Internet, or another type of data link. Furthermore, the information transferred between the diagnostic imaging system 510 and the treatment planning system 530 may be either pulled or pushed across the data link 560, such as in a remote diagnosis or treatment planning configuration. For example, a user may utilize embodiments of the present invention to remotely diagnose or plan treatments despite the existence of a physical separation between the system user and the patient.

The illustrated treatment planning system 530 includes a processing device 532, a system memory device 534, an electronic data storage device 536, a display device 538, and an input device 540. The processing device 532, system memory 534, storage 536, display 538, and input device 540 may be coupled together by one or more communication channel 542 such as a bus.

The processing device 532 receives and processes image data. The processing device 532 also processes instructions and operations within the treatment planning system 530. In certain embodiments, the processing device 532 may include one or more general-purpose processors (e.g., a microprocessor), special purpose processors such as a digital signal processor (DSP), or other types of devices such as a controller or field programmable gate array (FPGA).

In particular, the processing device 532 may be configured to execute instructions for performing the operations discussed herein. For example, the processing device 532 may be configured identifying a non-linear path of movement of the target based on the plurality of data points and the image using a parameterization function to approximate the non-linear path of movement. The processing device 532 may also be configured to execute instructions for performing other operations, such as, for example, the processing device 532 may a correlation model (e.g., constrained-curve correlation model) that maps movement of the external marker to a target location of the target using the parameterization function. In another embodiment, the processing device 532 may develop the constrained-curve correlation model based on one or more position points and multiple direction indicators. In another embodiment, the processing device 532 may generate multiple correlation models and select one of the models to derive a position of the target. Furthermore, the processing device 532 may facilitate other diagnosis, planning, and treatment operations related to the operations described herein.

In one embodiment, the processing device 532 is configured to perform the operations of the processing device 1302, as described above, such as to identifying a non-linear path of movement of the target based on the plurality of data points and the image using a parameterization function to approximate the non-linear path of movement.

In one embodiment, the system memory 534 may include random access memory (RAM) or other dynamic storage devices. As described above, the system memory 534 may be coupled to the processing device 532 by the communication channel 542. In one embodiment, the system memory 534 stores information and instructions to be executed by the processing device 532. The system memory 534 also may be used for storing temporary variables or other intermediate information during execution of instructions by the processing device 532. In another embodiment, the system memory 534 also may include a read only memory (ROM) or other static storage device for storing static information and instructions for the processing device 532.

In one embodiment, the storage 536 is representative of one or more mass storage devices (e.g., a magnetic disk drive, tape drive, optical disk drive, etc.) to store information and instructions. The storage 536 and/or the system memory 534 also may be referred to as computer readable media. In a specific embodiment, the storage 536 may store instructions to perform the modeling operations discussed herein. For example, the storage 536 may store instructions to acquire and store data points, acquire and store images, identify non-linear paths, develop linear and/or non-linear correlation models, select a correlation model from multiple models, and so forth. In another embodiment, the storage 536 may include one or more databases. In one embodiment, the data stored in the storage device 1303 of FIG. 13 is stored in either system memory 534 or storage 536.

In one embodiment, the display 538 may be a cathode ray tube (CRT) display, a liquid crystal display (LCD), or another type of display device. The display 538 displays information (e.g., a two-dimensional or three-dimensional representation of the VOI) to a user. The input device 540 may include one or more user interface devices such as a keyboard, mouse, trackball, or similar device. The input device(s) 540 may also be used to communicate directional information, to select commands for the processing device 532, to control cursor movements on the display 538, and so forth. In one embodiment, the display 538 and input device 540 are part of the user interface 1301, described above with respect to FIG. 13.

Although one embodiment of the treatment planning system 530 is described herein, the described treatment planning system 530 is only representative of an exemplary treatment planning system 530. Other embodiments of the treatment planning system 530 may have many different configurations and architectures and may include fewer or more components. For example, other embodiments may include multiple buses, such as a peripheral bus or a dedicated cache bus. Furthermore, the treatment planning system 530 also may include Medical Image Review and Import Tool (MIRIT) to support DICOM import so that images can be fused and targets delineated on different systems and then imported into the treatment planning system 530 for planning and dose calculations. In another embodiment, the treatment planning system 530 also may include expanded image fusion capabilities that allow a user to plan treatments and view dose distributions on any one of various imaging modalities such as MRI, CT, PET, and so forth. Furthermore, the treatment planning system 530 may include one or more features of convention treatment planning systems.

In one embodiment, the treatment planning system 530 may share a database on the storage 536 with the treatment delivery system 550 so that the treatment delivery system 550 may access the database prior to or during treatment delivery. The treatment planning system 530 may be linked to treatment delivery system 550 via a data link 570, which may be a direct link, a LAN link, or a WAN link, as discussed above with respect to data link 560. Where LAN, WAN, or other distributed connections are implemented, any of components of the treatment system 500 may be in decentralized locations so that the individual systems 510, 530, 550 may be physically remote from one other. Alternatively, some or all of the functional features of the diagnostic imaging system 510, the treatment planning system 530, or the treatment delivery system 550 may be integrated with each other within the treatment system 500.

The illustrated treatment delivery system 550 includes a radiation source 552, an imaging system 1305, a processing device 1302, and a treatment couch 558. The radiation source 552, imaging system 1305, processing device 1302, and treatment couch 558 may be coupled to one another via one or more communication channel 560. One example of a treatment delivery system 550 is shown and described in more detail with reference to FIG. 17.

In one embodiment, the radiation source 552 is a therapeutic or surgical radiation source 552 to administer a prescribed radiation dose to a target in conformance with a treatment plan. For example, the target may be an internal organ, a tumor, a region. For convenience, reference herein to the target or a target refers to any whole or partial organ, tumor, region, or other delineated volume that is the subject of a treatment plan.

In one embodiment, the imaging system 1305 of the treatment delivery system 550 captures intra-treatment images of a patient volume, including the target volume, for registration or correlation with the diagnostic images described above in order to position the patient with respect to the radiation source. Similar to the diagnostic imaging system 510, the imaging system 1305 of the treatment delivery system 550 may include one or more sources and one or more detectors, and a processing device, as described above with respect to FIG. 13.

The treatment delivery system 550 also may include the processing device 1302, as described in FIG. 13, to control the radiation source 552, the imaging system 1305, and a treatment couch 558, which is representative of any patient support device. The processing device 1302 may include one or more general-purpose processors (e.g., a microprocessor), special purpose processors such as a digital signal processor (DSP), or other devices such as a controller or field programmable gate array (FPGA). Additionally, the processing device 1302 may include other components (not shown) such as memory, storage devices, network adapters, and the like.

Figure 17:
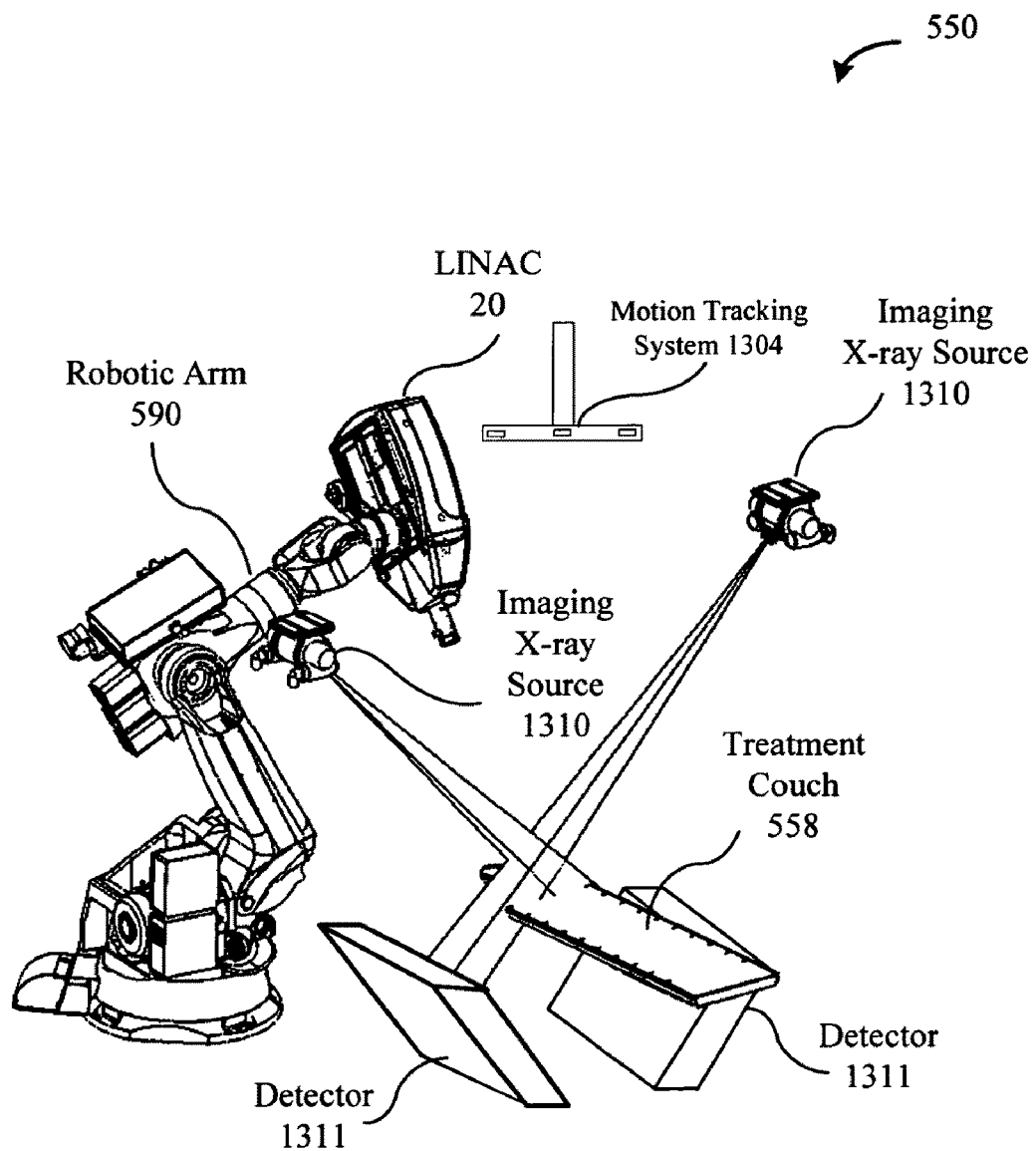
FIG. 17 is a schematic block diagram illustrating one embodiment of a treatment delivery system.

FIG. 17 is a schematic block diagram illustrating one embodiment of a treatment delivery system 550. The depicted treatment delivery system 550 includes a radiation source 552, in the form of a linear accelerator (LINAC) 20, and a treatment couch 558, as described above. The treatment delivery system 550 also includes multiple imaging X-ray sources 1310 and detectors 1311. The two X-ray sources 1310 may be nominally aligned to project imaging X-ray beams through a patient from at least two different angular positions (e.g., separated by 90 degrees, 45 degrees, etc.) and aimed through the patient on the treatment couch 558 toward the corresponding detectors 1311. In another embodiment, a single large imager may be used to be illuminated by each X-ray imaging source 1310. Alternatively, other quantities and configurations of imaging sources 1310 and detectors 1311 may be used. The depicted treatment delivery system 550 also includes the motion tracking system 1304 that tracks the motion of the external marker 25, as described above with respect to FIG. 13. In one embodiment, the treatment delivery system 550 may be an image-guided, robotic-based radiation treatment system (e.g., for performing radiosurgery) such as the CYBERKNIFE® system developed by Accuray Inc., Sunnyvale, Calif.

In the illustrated embodiment, the LINAC 20 is mounted on a robotic arm 590. The robotic arm 590 may have multiple (e.g., 5 or more) degrees of freedom in order to properly position the LINAC 20 to irradiate a target such as a pathological anatomy with a beam delivered from many angles in an operating volume around the patient. The treatment implemented with the treatment delivery system 550 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. In one embodiment, the treatment delivery system 550 delivers radiation beams according to the treatment plan without fixing the patient to a rigid, external frame to register the intra-operative position of the target volume with the position of the target volume during the pre-operative treatment planning phase.

As described above, the processing device 1302 may implement algorithms to register images obtained from the imaging system 1305 with pre-operative treatment planning images obtained from the diagnostic imaging system 510 in order to align the patient on the treatment couch 558 within the treatment delivery system 550. Additionally, these images may be used to precisely position the radiation source 552 with respect to the target volume or target.

In one embodiment, the treatment couch 558 may be coupled to second robotic arm (not shown) having multiple degrees of freedom. For example, the second arm may have five rotational degrees of freedom and one substantially vertical, linear degree of freedom. Alternatively, the second arm may have six rotational degrees of freedom and one substantially vertical, linear degree of freedom. In another embodiment, the second arm may have at least four rotational degrees of freedom. Additionally, the second arm may be vertically mounted to a column or wall, or horizontally mounted to pedestal, floor, or ceiling. Alternatively, the treatment couch 558 may be a component of another mechanism, such as the AXUM® treatment couch developed by Accuray Inc., Sunnyvale, Calif. In another embodiment, the treatment couch 558 may be another type of treatment table, including a conventional treatment table.

Although one exemplary treatment delivery system 550 is described above, the treatment delivery system 550 may be another type of treatment delivery system. For example, the treatment delivery system 550 may be a gantry based (isocentric) intensity modulated radiotherapy (IMRT) system, in which a radiation source 552 (e.g., a LINAC 20) is mounted on the gantry in such a way that it rotates in a plane corresponding to an axial slice of the patient. Radiation may be delivered from several positions on the circular plane of rotation. In another embodiment, the treatment delivery system 550 may be a stereotactic frame system such as the GAMMAKNIFE®, available from Elekta of Sweden.

Figure 18:
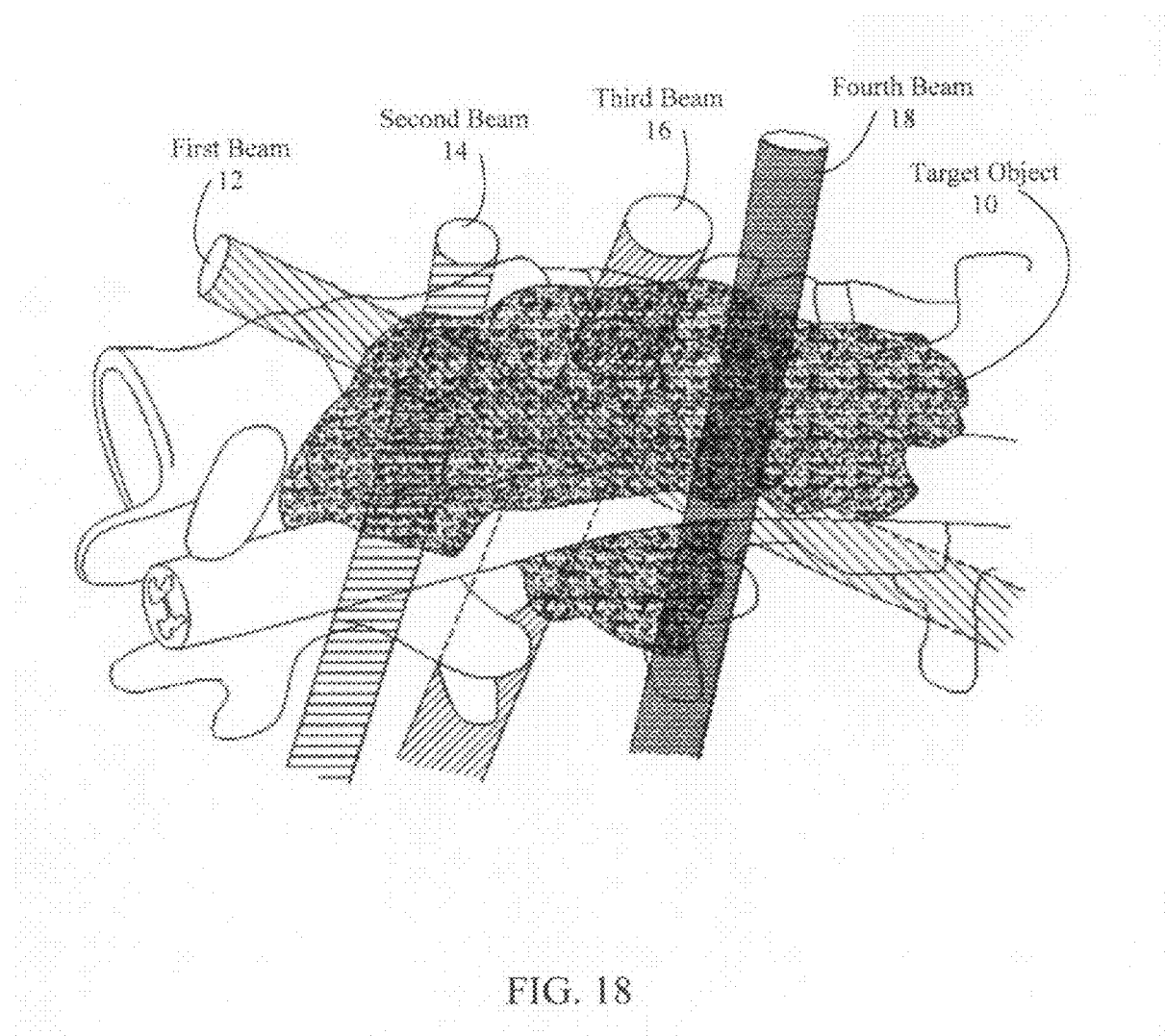
FIG. 18 illustrates a three-dimensional perspective view of a radiation treatment process.

FIG. 18 illustrates a three-dimensional perspective view of a radiation treatment process. In particular, FIG. 18 depicts several radiation beams directed at a target 10. In one embodiment, the target 10 may be representative of an internal organ, a region within a patient, a pathological anatomy such as a tumor or lesion, or another type of object or area of a patient. The target 10 also may be referred to herein as a target region, a target volume, and so forth, but each of these references is understood to refer generally to the target 10, unless indicated otherwise.

The illustrated radiation treatment process includes a first radiation beam 12, a second radiation beam 14, a third radiation beam 16, and a fourth radiation beam 18. Although four radiation beams 12-18 are shown, other embodiments may include fewer or more radiation beams. For convenience, reference to one radiation beam 12 is representative of all of the radiation beams 12-18, unless indicated otherwise. Additionally, the treatment sequence for application of the radiation beams 12-18 may be independent of their respective ordinal designations.

In one embodiment, the four radiation beams 12 are representative of beam delivery based on conformal planning, in which the radiation beams 12 pass through or terminate at various points within target 10. In conformal planning, some radiation beams 12 may or may not intersect or converge at a common point in three-dimensional space. In other words, the radiation beams 12 may be non-isocentric in that they do not necessarily converge on a single point, or isocenter. However, the radiation beams 12 may wholly or partially intersect at the target 10 with one or more other radiation beams 12.

In another embodiment, the intensity of each radiation beam 12 may be determined by a beam weight that may be set by an operator or by treatment planning software. The individual beam weights may depend, at least in part, on the total prescribed radiation dose to be delivered to target 10, as well as the cumulative radiation dose delivered by some or all of the radiation beams 12. For example, if a total prescribed dose of 3500 cGy is set for the target 10, the treatment planning software may automatically predetermine the beam weights for each radiation beam 12 in order to balance conformality and homogeneity to achieve that prescribed dose. Conformality is the degree to which the radiation dose matches (conforms to) the shape and extent of the target 10 (e.g., tumor) in order to avoid damage to critical adjacent structures. Homogeneity is the uniformity of the radiation dose over the volume of the target 10. The homogeneity may be characterized by a dose volume histogram (DVH), which ideally may be a rectangular function in which 100 percent of the prescribed dose would be over the volume of the target 10 and would be zero everywhere else.

The method described above offers many advantages, compared to currently know methods. A first advantage is that this method reduces the number of model points (e.g., images) needed to develop the correlation model, such as compared to conventional models that require six or more evenly-distributed model points, since the parameterization function that satisfies the four boundary conditions only has one unknown model parameter. A second advantage is that the number of unnecessary imaging occurrences is reduced, since the parameterization function only has one unknown model parameter. A third advantage is that the constrained curves do not have problems approximating the target locations at the boundary regions corresponding to moments between the inspiration and expiration periods, since the parameterization function satisfies the four boundary conditions described herein. By using a constrained curve that satisfies these four boundary conditions, the shape of the curves at the boundary regions is already determined as part of the correlation model. Also, by using a constrained curve that satisfies these four boundary conditions, no matching approximations or blending is required to link the inspiration and expiration approximations. Another advantage is that the constrained-curve correlation model can be easily adapted when a significant change in movement behavior is detected, for example, respiration behavior.

In sum, a method and system are presented for identifying a non-linear path of movement of the target based on the plurality of data points and the image using a parameterization function to approximate the non-linear path of movement. The above described method and system can detect and identify whether a patient's internal organ moves (during respiration of the patient) along different paths during the inspiration and the expiration phases of the respiration, respectively. The above-described method allows a correlation model to be constructed, which can accurately estimate the position of an internal organ that either undergoes non-linear movement, or moves along different paths during the inspiration and the expiration phases of the respiration, or both. Any other types of non-linear motion of an organ can also be fitted using the constrained-curve models as described above, by determining the one model parameter of the parameterization function that satisfies the four boundary conditions. The method described above permits the targeting of internal lesions and/or tumors that move with respiration (or other patient motion), for purpose of delivering therapeutic radiation to the lesions and tumors.

While the method and system above have been described in conjunction with respiratory motion of the patient, other embodiments may track asymmetric, curvilinear motion (or otherwise nonlinear) of the internal organs that occur during any other type of motion of the patient, e.g. heartbeat. Also, although some of the embodiments described below are directed to developing a correlation model with model points in a breathing waveform (e.g., respiratory cycle) to track movement of the target based on a patient's breathing, in other embodiments, the correlation model can be developed for other types of waveforms, such as heartbeat cycles of a patient, or other waveforms of other periodic motions of the patient.

While the constrained-curve correlation method and system have been particularly shown and described with reference to specific embodiments, it should be understood by those skilled in the art that various changes in form and detail may be made therein without departing from the spirit and scope of the invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by treatment planning software, such as the application of a beam (e.g., radiation, acoustic, etc.).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
  acquiring a plurality of data points representative of a corresponding plurality of positions over time of an external marker disposed on a surface of an object; acquiring an image of a target internal to the object; and identifying a non-linear path of movement of the target based on the plurality of data points and the image using a parameterization function to approximate the non-linear path of movement, wherein the parameterization function comprises a constrained curve that intersects a principal axis of the plurality of data points at a first intersection and at a second intersection, and the constrained curve is tangent to the principal axis at the first and second intersections, wherein the principal axis is determined using an approximation of the plurality of data points.

2. The method of claim 1, further comprising generating a correlation model that maps movement of the external marker to a target location of the target using the parameterization function.

3. The method of claim 2, wherein the parameterization function comprises only one model parameter, wherein the parameterization function satisfies four boundary conditions, comprising:
  a first boundary condition that the constrained curve intersects the principal axis at the first intersection;
  a second boundary condition that the constrained curve intersects the principal axis at the second intersection;
  a third boundary condition that the constrained curve is tangent to the principal axis at the first intersection; and
  a fourth boundary condition that the constrained curve is tangent to the principal axis at the second intersection.

4. The method of claim 3, further comprising:
  determining a first sample point of the target location using the acquired image; and determining a shape of the constrained curve using the parameterization function that satisfies the four boundary conditions and the first sample point, and wherein the first sample point defines an amount of curve of the constrained curve between the first and second intersections.

5. The method of claim 4, wherein the parameterization function is a fourth order polynomial, and wherein said determining the shape comprises
applying the four boundary conditions to the fourth order polynomial, wherein the fourth order polynomial is represented by the following equation:
$x=a\rho^4+b\rho^3+c\rho^2+d\rho+e$, where a, b, c, d, e are unknown model parameters and $\rho$ is a displacement of the target location,
wherein the fourth order polynomial is represented by the following equation after applying the four boundary conditions:
$x=a\rho^4-2a\rho^3+a\rho^2$, where a is the only unknown model parameter; and
applying the first sample point to the only unknown model parameter of the fourth order polynomial.

6. The method of claim 4, wherein the parameterization function is a sinusoid function having a power of two or more, wherein the sinusoid function inherently satisfies the four boundary conditions.

7. The method of claim 6, wherein the sinusoid function is represented by the following equation $x=a \sin^2 \rho$, where a is the only unknown model parameter and $\rho$ is a displacement of the target location, and wherein said determining the shape comprises applying the first sample point to the only unknown model parameter of the sinusoid function.

8. The method of claim 6, wherein the sinusoid function is represented by the following equation $x=a|\sin^3 \rho x|$, where a is the only unknown model parameter and $\rho$ is a displacement of the target location, and wherein said determining the shape comprises applying the first sample point to the only unknown model parameter of the sinusoid function.

9. The method of claim 6, wherein the sinusoid function is represented by the following equation $x=a \sin^4 \rho$, where a is the only unknown model parameter and $\rho$ is a displacement of the target location, and wherein said determining the shape comprises applying the first sample point to the only unknown model parameter of the sinusoid function.

10. The method of claim 2, further comprising:
identifying an inspiration interval of the non-linear path of movement of the target, the inspiration interval associated with an approximate time during which the patient breathes in; and
identifying an expiration interval of the non-linear path of movement of the target, the expiration interval associated with an approximate time during which the patient breathes out, wherein the non-linear path of movement of the target comprises:
an inspiration path associated with the inspiration interval; and
an expiration path associated with the expiration interval, wherein the plurality of positions of the external marker defines an external path of movement of the external marker, the external path of movement having a respiratory period associated with a respiratory cycle of the patient, and wherein a derivative of the plurality of data points at a selected one of the plurality of data points identifies an inspiration interval and a expiration interval of the respiratory period, the derivative comprising a directional indicator.

11. The method of claim 10, wherein the correlation model comprises a dual-constrained-curve model, wherein the dual-constrained-curve model comprises:
a first constrained curve associated with the non-linear path of movement of the target over the inspiration interval; and
a second constrained curve associated with the non-linear path of movement of the target over the expiration interval.

12. The method of claim 2, further comprising deriving a target position of the target based on the correlation model.

13. The method of claim 2, further comprising:
detecting a change in magnitude of the movement of the external marker; and
automatically scaling the correlation model when a change in magnitude of the movement of the external marker is detected.

14. The method of claim 12, further comprising:
sending a position signal associated with the target position to a beam generator controller; and
controlling a beam generator to direct a beam at the target.

15. The method of claim 1, further comprising updating the correlation model in response to an acquisition of a new image.

16. An apparatus, comprising:
an data storage device to store a plurality of displacement points of an external marker and a corresponding plurality of images of a target; and
a processing device coupled to the data storage device, the processing device to identify a non-linear path of movement of the target using a parameterization function to approximate the non-linear path of movement, wherein the parameterization function comprises a constrained curve that intersects a principal axis of the plurality of data points at a first intersection and at a second intersection, and the constrained curve is tangent to the principal axis at the first and second intersections, wherein the principal axis is determined using an approximation of the plurality of data points.

17. The apparatus of claim 16, wherein the processing device is further configured to develop a correlation model of the non-linear path of movement using the parameterization function based on the plurality of data points and at least one of the plurality of images, wherein the parameter approximation function satisfies four boundary conditions, comprising:
a first boundary condition that the constrained curve intersects the principal axis at the first intersection;
a second boundary condition that the constrained curve intersects the principal axis at the second intersection;
a third boundary condition that the constrained curve is tangent to the principal axis at the first intersection; and
a fourth boundary condition that the constrained curve is tangent to the principal axis at the second intersection.

18. The apparatus of claim 16, wherein the processing device is configured to receive a first acquired image of the plurality of images, to determine a first sample point, and to determine a shape of the constrained curve using the parameterization function and the first sample point, wherein the first sample point defines an amount of curve of the constrained curve between the first and second intersections.

19. The apparatus of claim 16, wherein the parameterization function is a fourth order polynomial that has only one unknown model parameter, wherein the fourth order polynomial is: $x=a\rho^4-2a\rho^3+a\rho^2$, where a is the one unknown model parameter and $x=a\rho^4-2a\rho^3+a\rho^2$.

20. The apparatus of claim 16, wherein the parameterization function is a sinusoid function having a power of two or more, wherein the sinusoid function inherently satisfies the four boundary conditions.

21. The apparatus of claim 16, wherein the processing device is configured to detect a change in magnitude of the movement of the external marker, and to scale the correlation model when the change in magnitude of the movement of the external marker is detected.

22. An apparatus, comprising:
means for receiving a plurality of data points representative of a corresponding plurality of positions over time of an external marker disposed on a surface of an object;
means for receiving an image of a target internal to the object; and
means for reducing a number of images acquired in developing a correlation model that maps the movement of the external marker to a target location of the target, wherein reducing a number of images acquired developing the correlation model that includes only one unknown model parameter, which is one sample point.

23. The apparatus of claim 22, further comprising
means for detecting a change in magnitude of the movement of the external marker; and
means for automatically scaling the correlation model when the change in magnitude of the movement of the external marker is detected.

24. A non-transitory computer readable medium having instructions thereon, which when executed by a processing device, cause the processing device to perform the following operations comprising:
receiving a plurality of displacement points over time of an external marker attached to a body;
receiving a image of a target internal to the body; and
developing a correlation model based on the plurality of displacement points and the image using a parameterization function that includes a constrained curve that intersects a principal axis of the plurality of data points at a first intersection and at a second intersection, and the constrained curve is tangent to the principal axis at the first and second intersections, wherein the correlation model maps the movement of the external marker to a target location of the target, wherein the principal axis is determined using an approximation of the plurality of data points.

* * * * *